(12) United States Patent
Wijffels

(10) Patent No.: US 8,042,992 B2
(45) Date of Patent: Oct. 25, 2011

(54) SENSOR FOR THERMAL ANALYSIS AND SYSTEMS INCLUDING SAME

(75) Inventor: Martinus J. L. M. Wijffels, Vught (NL)

(73) Assignees: Anatech B.V., KN Sittard (NL); PerkinElmer LAS, Inc., Waltham, MA (US)

( * ) Notice: Subject to any disclaimer, the term of this patent is extended or adjusted under 35 U.S.C. 154(b) by 523 days.

(21) Appl. No.: 12/058,921

(22) Filed: Mar. 31, 2008

(65) Prior Publication Data

US 2009/0052494 A1  Feb. 26, 2009

Related U.S. Application Data

(60) Provisional application No. 60/909,019, filed on Mar. 30, 2007.

(51) Int. Cl.
*G01N 25/00* (2006.01)
*G01K 17/00* (2006.01)
*G01K 1/00* (2006.01)

(52) U.S. Cl. ............... 374/12; 374/14; 374/31; 374/29; 374/208

(58) Field of Classification Search ............ 374/31, 374/10, 12, 14, 208, 29
See application file for complete search history.

(56) References Cited

U.S. PATENT DOCUMENTS

| | | | |
|---|---|---|---|
| 3,491,581 A * | 1/1970 | Harlan et al. | 374/12 |
| 5,356,217 A | 10/1994 | Sheffield | |
| 7,141,812 B2 | 11/2006 | Appleby | |
| 2005/0233062 A1 | 10/2005 | Hossainy | |
| 2010/0303124 A1 * | 12/2010 | Ellison et al. | 374/31 |

OTHER PUBLICATIONS

International Search Report and Written Opinion for PCT/US2008/58856.

* cited by examiner

*Primary Examiner* — Lisa Caputo
*Assistant Examiner* — Mirellys Jagan
(74) *Attorney, Agent, or Firm* — Lando & Anastasi, LLP

(57) ABSTRACT

Certain embodiments disclosed herein are directed to a sensor comprising a support member, a sample sensor coupled to the support member and comprising a sample support electrically coupled to a first set of interconnects, and a reference sensor coupled to the support member and comprising a ring coupled to a second set of interconnects, in which the ring is positioned adjacent to and surrounding at least a portion of the sample support of the sample sensor.

19 Claims, 24 Drawing Sheets

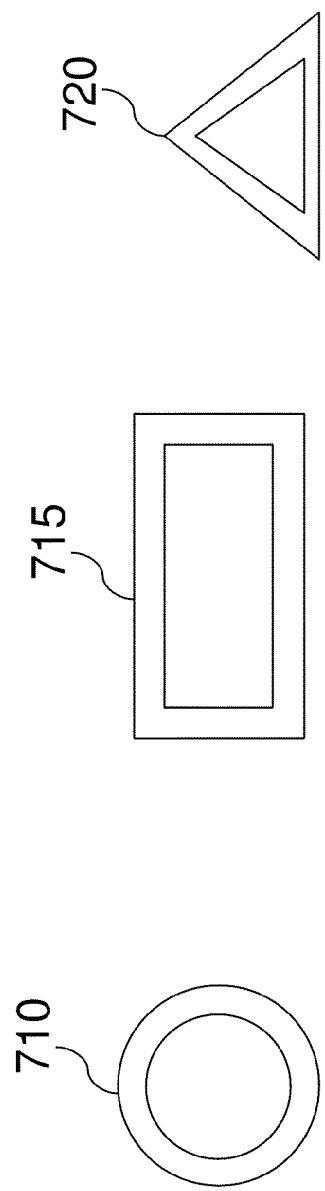
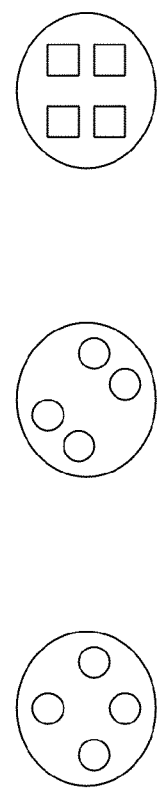

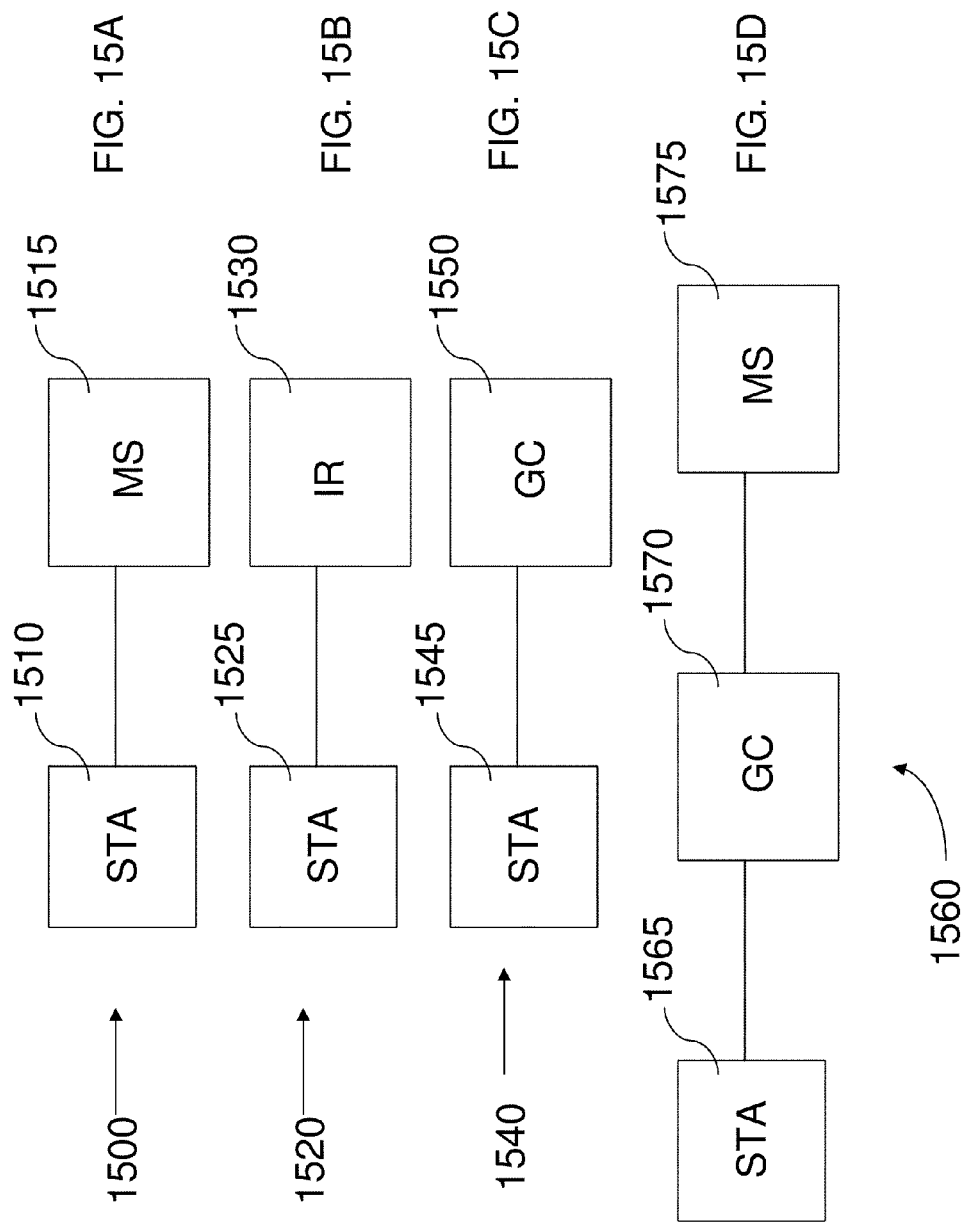

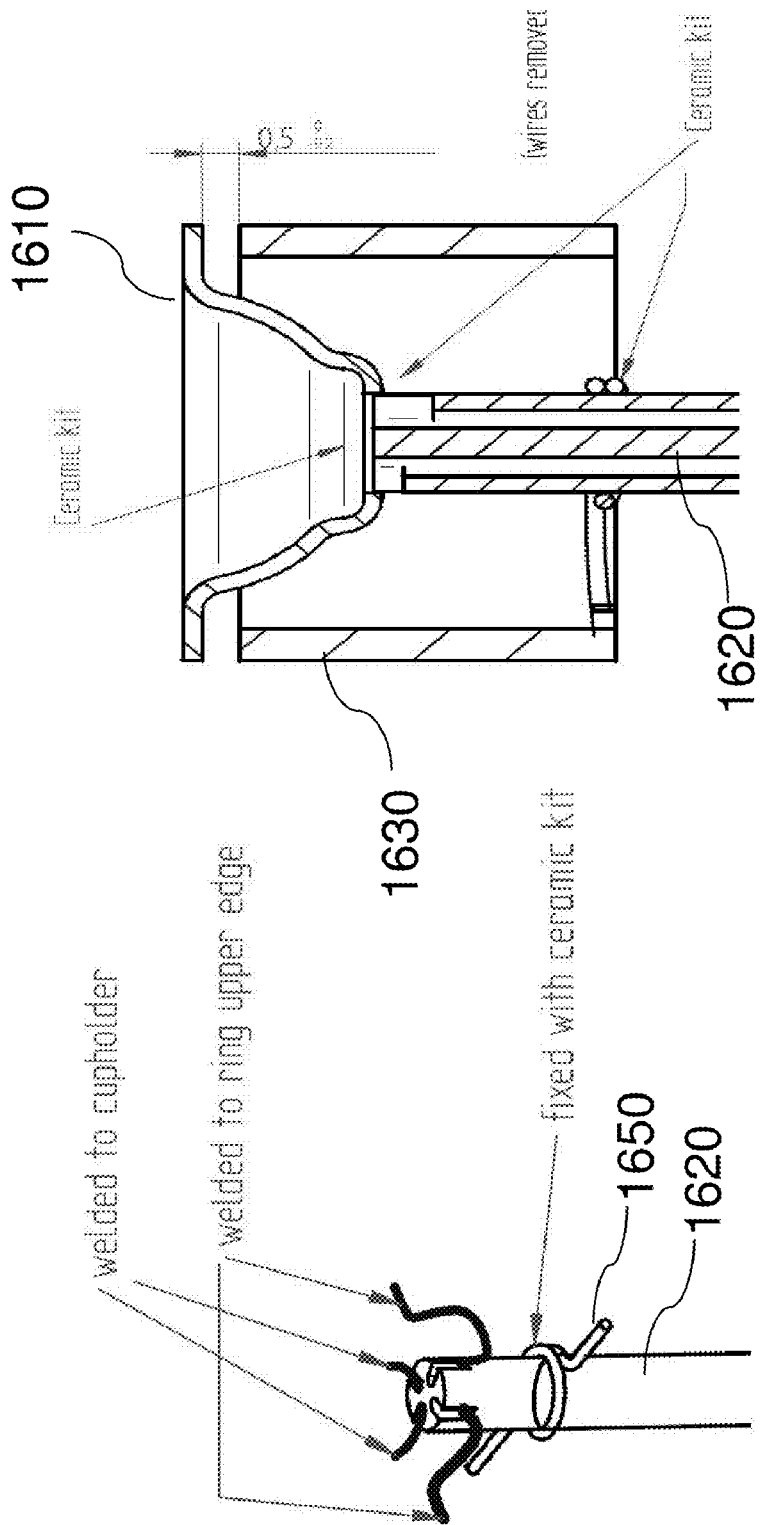

SENSOR FOR THERMAL ANALYSIS AND SYSTEMS INCLUDING SAME

PRIORITY APPLICATION

This application claims priority to, and the benefit of, U.S. Provisional Application No. 60/909,019 filed on Mar. 30, 2007, the entire disclosure of which is hereby incorporated herein by reference for all purposes.

TECHNOLOGICAL FIELD

Certain embodiments disclosed herein relate generally to sensors for use in thermal analysis. More particularly, certain examples disclosed herein relate to a thermal analysis sensor that may include a sample sensor and a reference sensor.

BACKGROUND

Thermal Analysis, or "TA", describes a series of techniques to characterize a sample, or one or more physical properties of the sample, with relation to temperature, by applying a controlled temperature to the sample. Simultaneous Thermal Analysis ("STA") instruments, otherwise known as Thermogravimetry/Differential Thermal Analysis ("TGA/DTA") instruments, often use two discrete, symmetrical sample and reference crucibles or pans for analysis. The two crucibles are heated and/or cooled at a precisely controlled rate in a controlled environment. Differences in the thermal behavior of the sample caused by differences in specific heat, occurrence of an exothermic or endothermic reaction, or a phase change, can result in a temperature difference between the two crucibles that can be measured and used to characterize the sample.

SUMMARY

In one aspect, a sensor comprising a support member, a sample sensor and reference sensor. In some examples, the sample sensor may be coupled to the support member and comprise a sample support electrically coupled to a first set of interconnects. In certain embodiments, a reference sensor coupled to the support member and comprises a ring coupled to a second set of interconnects, in which the ring is positioned adjacent to and surrounding at least a portion of the sample support of the sample sensor.

In certain examples, the sensor may further comprise a connector coupled to the support member, the connector configured to couple the sensor to a balance. In other examples, the sensor may further comprise a controller coupled to the first set of interconnects and the second set of interconnects. In additional examples, the ring of the reference sensor may be a cylindrical ring with an inner surface positioned less than 0.5 mm from an outer surface of the sample support. In some examples, the ring comprises an outer diameter of about 7 mm and an inner diameter of about 6 mm. In certain embodiments, the sample support and the ring of the reference sensor are both platinum. In some embodiments, the reference sensor may be configured to provide a reference signal without the addition of an external reference material. In some examples, the sample support comprises a concave surface configured to receive a crucible comprising a sample.

In an additional aspect, a sensor configured to provide temperature sensing using a sample sensor and a reference sensor is provided. In some examples, the sensor comprises a sample support with an outer surface positioned less than or equal to 0.5 mm from an inner surface of the reference sensor. In certain examples, the sample support and the reference sensor may comprise the same material. In some examples, the sample support comprises a concave surface configured to receive a crucible comprising a sample. In other examples, the outer surface of the sample support may be positioned about 0.25 mm from the inner surface of the reference sensor. In some examples, the reference sensor may comprise a cylindrical ring and be operative to provide a reference signal without the addition of an external reference material. In certain examples, the sensor ay further comprise a first set of interconnects electrically coupled to the sample support and a second set of interconnects electrically coupled to the reference sensor.

In another aspect, a system for simultaneous thermal analysis is disclosed. In certain examples, the system comprises a heating system comprising a furnace thermally coupled to a sensor comprising a support member, a sample sensor coupled to the support member and comprising a sample support electrically coupled to a first set of interconnects, and a reference sensor coupled to the support member and comprising a ring coupled to a second set of interconnects, in which the ring is positioned adjacent to and surrounding at least a portion of the sample support of the sample sensor. In some examples, the system may further comprise a controller coupled to the heating system and configured to receive signals from the first and second set of interconnects of the sensor.

In certain embodiments, the system may further comprise a gas control system coupled to the heating system. In some embodiments, the system may further comprise a balance coupled to the sensor. In other embodiments, the system may be configured for gravimetric analysis and at least one of differential thermal analysis and differential scanning calorimetry. In certain examples, the system may further comprise an analytical device coupled to the simultaneous thermal analysis system, the analytical device selected from the group consisting of a mass spectrometer, an infrared spectrometer, a gas chromatograph and combinations thereof. In some examples, the system may further comprise a computer system coupled to the simultaneous thermal analysis system. In additional examples, the system may further comprise an autosampling system coupled to the heating system.

In an additional aspect, a method of measuring thermal properties of a sample is provided. In some examples, the method comprises placing a sample on a sample support of a sensor in a furnace, the sensor comprising a sample support and a reference sensor adjacent to and surrounding at least a portion of the sample support, altering the temperature in the furnace to promote a physical or chemical change in the sample, and measuring the physical or chemical change in the sample using the sample sensor and the reference sensor.

In certain embodiments, the method may further comprise measuring the physical or chemical change without adding an external reference material to the reference sensor. In some examples, the method may further comprise measuring a change in mass of the sample and a change in temperature of the sample during the temperature altering step.

In another aspect, a method of facilitating measurement of thermal properties of a sample is disclosed. In certain examples, the method comprises providing a sensor configured with a support member, a sample sensor coupled to the support member and comprising a sample support electrically coupled to a first set of interconnects, and a reference sensor coupled to the support member and comprising a ring coupled to a second set of interconnects, in which the ring is positioned adjacent to and surrounding at least a portion of the sample support of the sample sensor.

In an additional aspect, a method of facilitating measurement of thermal properties of a sample comprising providing a sensor configured to provide temperature sensing using a sample sensor and a reference sensor, the sensor comprising a sample support with an outer surface positioned less than or equal to 0.5 mm from an inner surface of the reference sensor is provided.

Additional aspects, features, examples and embodiments are discussed in more detail below.

BRIEF DESCRIPTION OF THE FIGURES

Certain illustrative features and examples are described below with reference to the accompanying figures in which:

FIG. 7A-7C show various reference sensor geometries that may be used, in accordance with certain examples;

FIGS. 8A-8C is a cross-section of support members showing the channels configured to receive the interconnects, in accordance with certain examples;

FIGS. 15A-15D are block diagrams showing illustrative hyphenated systems for use in thermal analysis, in accordance with certain examples;

FIG. 17A is a perspective view of the support components of a sensor, in accordance with certain examples;

FIG. 17B is a cross-section of an assembled sensor, in accordance with certain examples;

Figure 1:
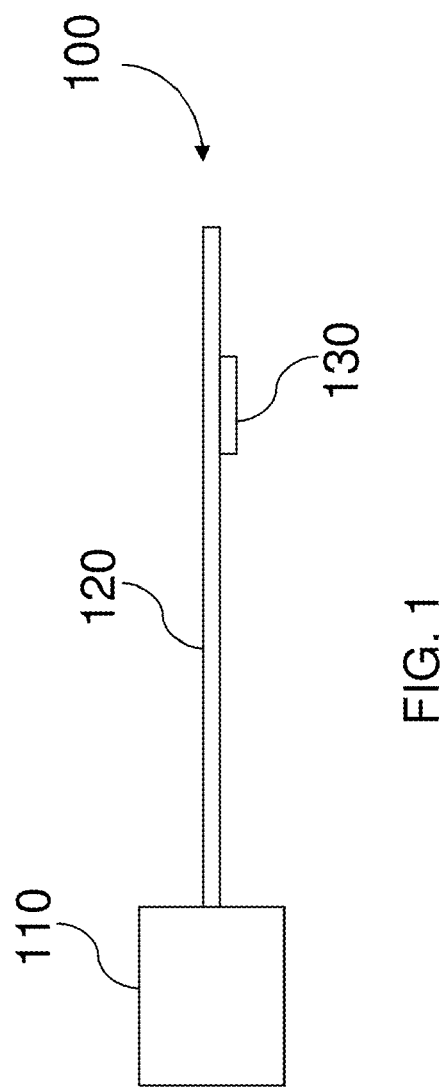
FIG. 1 is a side-view of a sensor, in accordance with certain examples.

It will be recognized by the person of ordinary skill in the art, given the benefit of this disclosure, that the dimensions, sizes, components and views shown in the figures for the sensors are provided for illustrative purposes. Other dimensions, representations, features and components may also be included in the sensors disclosed herein without departing from the scope of this description.

DETAILED DESCRIPTION

Certain illustrative embodiments are described below to illustrate some of the uses, advantages and features of the technology described herein. Some embodiments of the sensors disclosed herein provide significant advantages over existing sensors for thermal analysis including, but not limited to, an integral sample and reference sensor, permitting a smaller footprint for a thermal analysis device using the sensor, improved thermal analysis measurements, higher sample throughput using automation, the ability to have a reference sensor that is operative without the addition of an external reference material and the like. By producing a sensor that includes an integrated sample and reference sensor, heat may be provided to the sample and reference sensors in a substantially equal way even though the sample and reference sensors operate independently of each other. Additional features and advantages for a particular illustration or embodiment of the sensors disclosed herein will be readily selected by the person of ordinary skill in the art, given the benefit of this disclosure. The sensors and systems implementing them that are disclosed herein may be used to analyze numerous different types of samples including polymers, foods, metals and other materials.

In certain examples, the sensors disclosed herein may be referred to in certain instances as a single stem or an integrated sensor. A "single stem" sensor, as used herein, refers to a sensor that includes a sample sensor and a reference sensor that are generally coaxial. In some examples, the single stem sensor includes a support member that does not split or bifurcate into two or more arms or portions along the length of the support member. A single stem sensor typically includes a single cylindrical rod-like support member coupled to a sample support and a reference sensor, though the sample support and the reference sensor are typically not coupled to each other. Such sensors may also include a single sample support designed to receive a sample, and a reference sensor surrounding at least some portion of the sample support and operative without the receipt or use of any externally added reference material. An inner surface of the reference sensor is typically positioned adjacent to an outer surface of the sample support, without the surfaces physically contacting each other, such that the reference sensor and sample support experience substantially the same thermal environment provided, for example, by a furnace. In some embodiments, it may be desirable to position the reference sensor as close as possible to the sample sensor without the surfaces physically contacting each other or electrically interfering with operation of the sensors.

In some examples, the exact dimensions and sizes of the reference sensor and sample support may vary, and in some examples, each of the reference sensor and sample support may be sized and arranged such that the thermal mass of the reference sensor is matched to the thermal mass of the sample support and/or any crucible containing a sample on the sample support. Illustrative shapes and dimensions are discussed below.

Certain embodiments of the technology disclosed herein relate to a sensor that can be used in simultaneous thermal analysis (STA) instruments. STA instruments typically implement two or more thermal analysis techniques, such as the illustrative thermal analysis methods described below. As used herein, "thermal analysis" refers to a large group of analytical measurements that either measure or use heat or temperature during some portion of the analysis. Illustrative thermal analysis techniques for use with the sensors disclosed herein are discussed in more detail below. The sensors disclosed herein may also be used in other instruments desiring the properties and features disclosed herein. Certain examples of the sensors disclosed herein provide a fixed, static reference sensor that can be mounted vertically on a single stem and includes a single sample support for accepting, for example, a single crucible (containing a sample), thereby eliminating the need for a reference (or second) crucible. The reference sensor may also serve or operate as a reference temperature thermocouple, thereby allowing the sensor and stem assembly to occupy less horizontal space than traditional sensors which employ dual crucibles. The physical characteristics of the reference sensor, including but not limited to the material, dimensions, and mounting location, are desirably designed to match, be substantially equivalent to, and/or replicate the thermal characteristics of the sample crucible and/or the sample support In certain embodiments, the sample sensor and the reference sensor may each be configured such that they are in, or experience or are exposed to, substantially the same thermal environment for at least some portion of a thermal analysis run. By placing the sample sensor and the reference sensor in close proximity to each other, any errors in temperatures and differences in heat exposure that may result due to the sensors being located in different physical positions may be reduced, as compared to dual or multi-stem sensors with the sample and reference sensors positioned on different support or different arms of a support.

Figure 2:
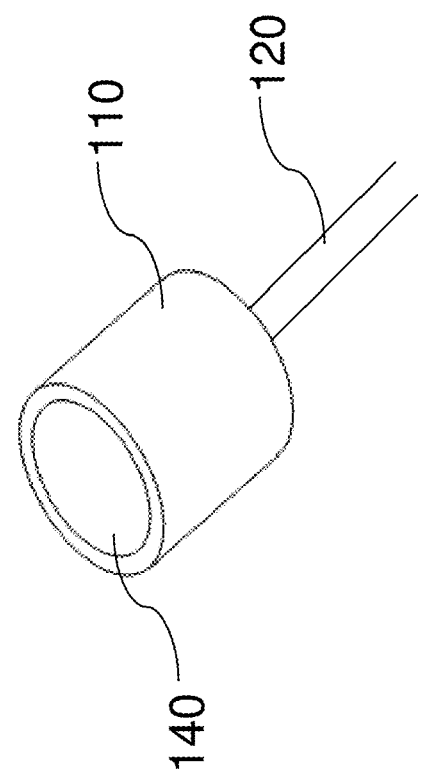
FIG. 2 is a perspective view of the sensor of FIG. 1, in accordance with certain examples.

In certain examples, the sensor may be configured with a sample support, a reference sensor, a support member and optionally a connector. One illustration of such a device is shown in FIGS. 1 and 2. In the side view shown in FIG. 1, the sensor 100 comprises a reference sensor 110, a support member 120 coupled to the reference sensor 110 and a connector 130 on, or coupled to, the support member 120. The sample support 140 (FIG. 2) may be coupled to a distal end of the support member 120 opposite the end near the connector 130. By including the sample sensor and the reference sensor in close proximity and coupled to a single support member, the overall size of the sensor may be reduced, which permits reduction in the size of analytical devices using the sensor. For example, the dimensions of a furnace to be used to provide heat to the sensor may be reduced. In addition, the close proximity of the sensors may reduce thermal anomalies that can result using dual or multi-stem sensing devices.

Figure 3:
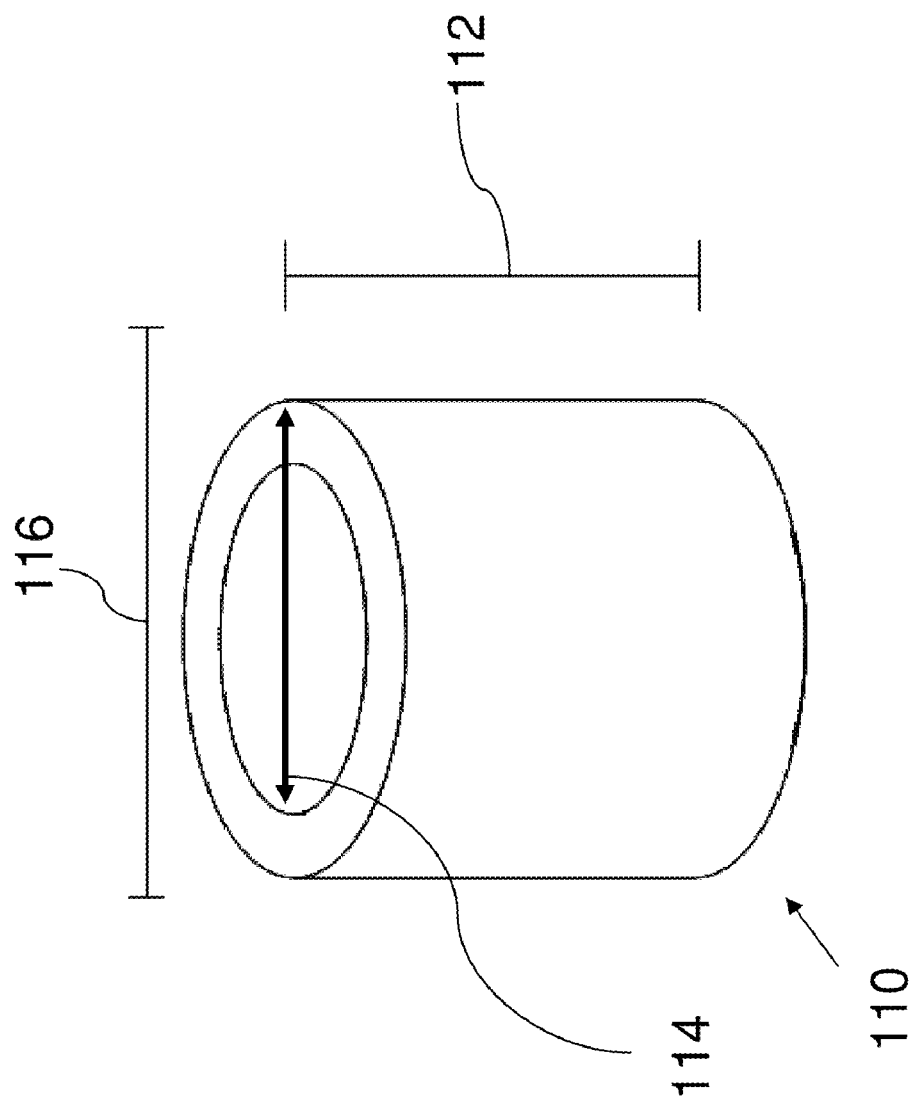
FIG. 3 is a cross-section of a perspective view of a reference sensor, in accordance with certain examples.

In some examples, the reference sensor 110 may take the form of a hollow, generally cylindrical shaped device that is configured to surround, but not physically contact, some portion or all of the sample support 140. For example, the reference sensor 110 may have a length 112, an inner diameter 114 and an outer diameter 116, as shown in FIG. 3. Illustrative dimensions for the reference sensor include but are not limited to, about 3-7 mm long, for example about 5 mm long, an inner diameter of about 5-7 mm, for example about 6 mm, and an outer diameter of about 6-8 mm, for example about 7 mm. While the reference sensor 110 is shown as cylindrical in FIGS. 2 and 3 other cross-sectional shapes may be used, as discussed further below.

In certain examples, the sample support 140 may sit or be suspended within the inner diameter of the reference sensor 110 such that an inner surface of the reference sensor 110 and an outer surface of the sample support 140 are placed a desired distance apart. In embodiments where the sample support 140 is circular and the reference sensor 110 is cylindrical, the spacing between the inner surface of the reference sensor 110 and the outer surface of the sample support 140 may be substantially the same around the circumference of the sample support. The sample support 140 may be configured as a lid, pan or support device that can be placed atop or near the top of the reference sensor 110 and coupled to one or more components of the sample sensor such as, for example, electrical connections that may be used to sense changes in heat or temperature. The sample support 140 may be in physical contact with the support member 120 such that the support member 120 positions the sample support 140 at a desired position relative to the position of the reference sensor 110. The sample support 140 may be configured to receive a sample such as, for example, a sample in a crucible or other suitable device. In some examples, the sample itself may be placed on the sample support 140, whereas in other examples, the sample may reside in a crucible which is placed on the sample support 140. In instances where a crucible containing a sample is placed on the sample support 140, the sample support 140 and the crucible are typically in thermal communication such that changes in temperature or changes in thermal properties from the sample may be sensed using the sample sensor. In some examples, the thermal properties of the sample support closely match or are similar to those of the crucible. The sample support 140 may be electrically coupled to leads or interconnects, which together can function as a thermocouple to sense changes in temperature of the sample. Illustrative thermocouples are discussed in more detail herein. The sample support and the interconnects form a sample sensor that can be used to detect physical or chemical changes in a sample that may occur during heating and/or cooling.

Figure 4A:
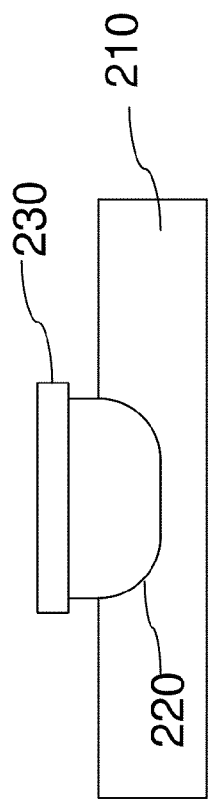
FIGS. 4A-4E are cross-sections of a side view of a sample support showing a crucible placed on the sample support, in accordance with certain examples.
Figure 4B:
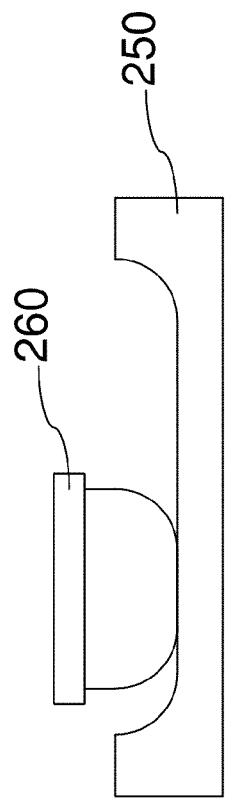
Figure 4C:
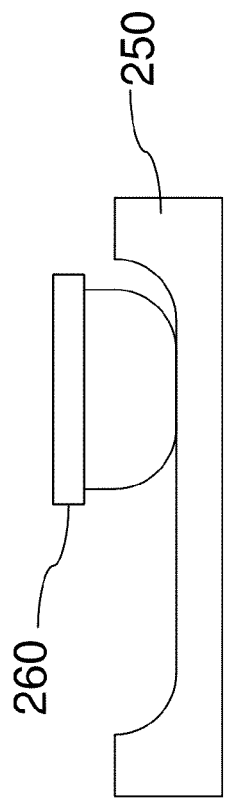
Figure 4E:
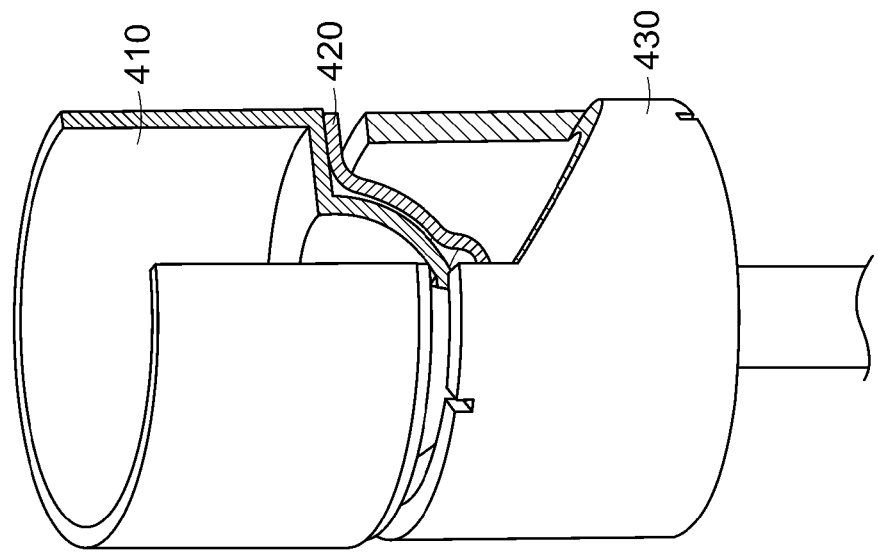
Figure 4D:
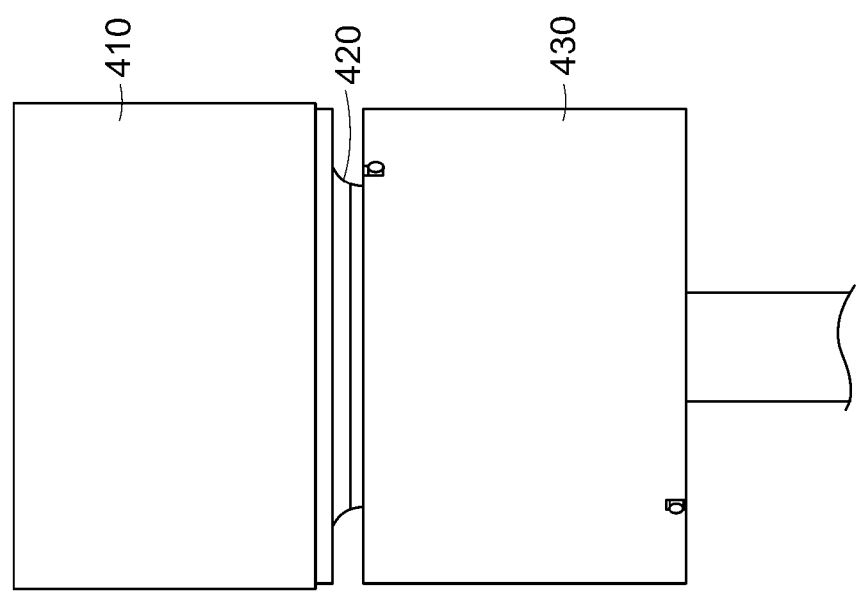

In some examples, the sample support may include a depression or concave surface such that a sample, or crucible containing a sample, may be held in place or contact with the sample support during one or more analytical measurements. In some examples, the concave surface may be sized and arranged to receive a crucible in a similar location each time, whereas in other examples, the crucible may be placed at any location along the sample support 140. For example and referring to FIG. 4A, a sample support 200 comprises a concave surface 220 that is configured to receive and retain a crucible 230 comprising a sample (not shown). The embodiment in FIG. 4A permits placement of the crucible in substantially the same position from measurement to measurement to increase the overall precision of the thermal analysis device. However, such placement may not be critical to precise and accurate measurements. In such instances, it may be desirable to use a sample support having an expanded concave surface such as, for example, the sample support 250 that is shown as retaining a crucible 260 in FIGS. 4B and 4C, where the exact placement of the crucible 260 along the concave surface varies. In some examples, the surface of the sample support may have one or more convex or protruding surfaces or other shapes depending on the desired construction and shape of the sample support and the crucible or other device used to provide or supply the sample itself. In use, the concave surface of the sample support typically is positioned horizontal, with the support member coupled to the sample support at a bottom surface. Referring to FIGS. 4D and 4E, a schematic of a crucible 410, sample support 420 and reference sensor 430 is shown. The crucible 410 has been placed in the sample support 420. As can be seen in the cut away view of FIG. 4E, the bottom of the crucible 410 sits on the base of the sample support 420 and does not contact the reference censor 430. The sample support 420 shown in FIGS. 4D and 4E provides for similar positioning of the crucible from run-to-run, which may reduce aberrations that result from slight differences in position of the crucible. In addition, it is desirable to use a sample support similar to, or the same as, the sample support 420 with an autosampler to facilitate receipt and safe handling of sample crucibles from the autosampler.

Figure 5:
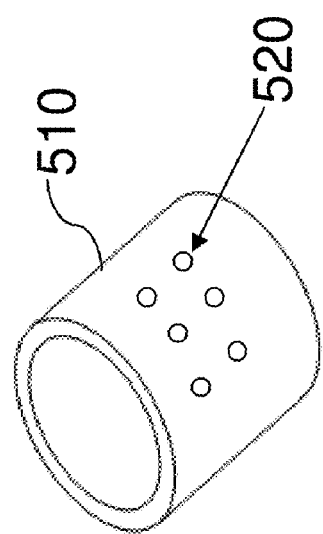
FIG. 5 shows an embodiment of a reference sensor including apertures for permitting heat entry, in accordance with certain examples.

In some examples, the sample support may include one or more stand-offs, bosses, spacers or the like to position the sample support a desired height or at a desired position. In other examples, the sample support and/or the reference sensor may include apertures or through holes to permit heat entry. For example and referring to FIG. 5, apertures or through-holes, such as aperture 520, may be cut or drilled into the reference sensor 510 such that heat is permitted to enter and exit from the reference sensor 510. In some examples, such apertures may be uniformly spaced or positioned along the surfaces to permit substantially equal heat flow into and out of the sensor. By permitting heat entry into and out of the sensor through one or more apertures, the thermal environment experienced by the reference sensor and the sample sensor may be substantially the same. The number and size of the apertures is not critical and illustrative numbers include, but are not limited to, one or more, for example, one to about thirty. Such through-holes may be on any surface or side of the reference sensor and/or the sample support, and in some examples, the through-holes are on both the reference sensor and the sample support.

In certain examples, the sample support may be constructed of materials similar to those used to construct the reference sensor such that the thermal properties are substantially similar to the thermal properties of the reference sensor and/or the thermal properties of a crucible comprising a sample to be analyzed. For example, the sample support may be made from metals, ceramics or other materials whose thermal properties are known or may be determined. Illustrative materials for use in the sample support include, but are not limited to, platinum, rhodium, rhenium, palladium, iridium, tungsten, gold, copper, silver, alumina, zirconia, yttria and mixtures of these illustrative materials. In some examples, a corrosion resistant coating may be deposited on the sample support to prevent etching or degradation of the sample support and to otherwise extend its useful operation life. It is desirable, though not required, to construct the reference sensor and the sample support from the same material or materials.

Figure 6:
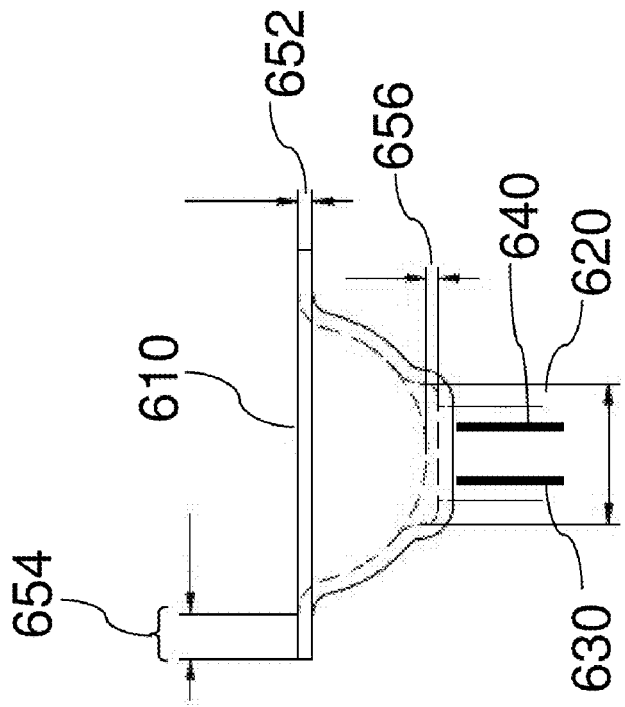
FIG. 6 is a cross section of a side view showing a sample support, in accordance with certain examples.

In some embodiments, interconnects may be sized and arranged such that connection of the sample support to the interconnects does not interference with positioning of the sample support along the support member. For example and referring to FIG. 6, a sample support 610 is shown as positioned on top of a support member 620. Interconnects 630 and 640 pass through the support member 620 and are coupled to a surface of the sample support 610. The interconnects typically attach to the base of the sample support and are not directly in the sample material itself. In an alternative embodiment, one or more support wires or structures may be used to elevate the sample support 610 a desired distance above the support member 620. In some examples, the interconnects 630 and 640 each have a length of about 70 mm to about 110 mm, more particularly, about 75 mm to about 100 mm. In certain examples, the thickness of the interconnects may vary from about 0.1 mm to about 0.3 mm, more particularly about 0.15 mm to about 0.25 mm, for example about 0.2 mm. As discussed in more detail below, the interconnects may generally run through or be routed through the support member 620 and electrically coupled to an analytical device, processor or other device that can receive and/or process signals from the sensors. In certain examples, the interconnects 630 and 640 may be made from, or include, a conductive material such as platinum or the like such that changes in temperature of the sample support 610, which are representative of changes in the temperature of the sample itself, may be sensed using the interconnects 630 and 640. Illustrative materials are discussed in more detail below in reference to materials used in thermocouples. Any one or more of these materials may independently be used to provide the interconnects 630 and 640.

In some examples, a lip of the sample support 610 may have a thickness 652 of about 0.1 mm to about 0.3 mm, for example about 0.25 mm. In some examples, the distance 654 from an outer surface of the sample support 610 to the portion that becomes concave is about 0.6 mm to about 1 mm, for example about 0.8 mm. The base of the sample support 610 may have a thickness 656 of about 0.1 mm to about 0.3 mm, for example, about 0.2 mm. The sample support 620 may have an inner diameter of about 1.0 mm to about 2.0 mm, for example about 1.6 mm and an outer diameter of about 1.6 mm to about 3.2 mm, for example, about 2.4 mm. Depending on the materials used, however, the exact dimensions of the sample support 610 and support member 620 may vary.

In certain examples, the interconnects may be coupled to the sample support in numerous manners using numerous materials. In particular, the exact methodology or technique used to couple the interconnects to the sample support, or the reference sensor, is not critical so long as the desired components to be coupled may be in electrical communication. For example, the interconnects may be soldered to the sample support, laser welded to the sample support, resistance welded to the sample support, glued or otherwise adhered to the sample support using a suitable adhesive or epoxy or may otherwise be attached to the sample support such that an electrical connection is provided between the sample support and the interconnects. In some examples, it is desirable to weld the interconnects to the sample support using substantially similar materials to those present in the interconnects or leads connected to the sample support.

In some examples, the exact configuration and placement of the reference sensor may vary. In some examples, the reference sensor may take the form of a disk, ring or toroid whose thermal properties may be matched to the thermal properties of the crucible and/or the sample support. For example, the reference sensor (when viewed from the top or bottom) may be shaped similar to a ring 710 (FIG. 7A), a rectangle 715 (FIG. 7B), a triangle 720 (FIG. 7C) or other suitable geometric shapes. The exact shape of the reference sensor is not critical, and any shape may be used where the thermal properties of such a shape provide a desired thermal response. In some examples, the inner cross-sectional shape may differ from the cross-sectional shape of the outer part of the reference sensor. In certain examples where the reference sensor takes the form of a ring, an inner surface of the ring may be mounted about 0.1 mm (or less) to about 2 mm from an outer surface of a reference sensor, more particularly about 0.25 to about 0.5 mm. Additional variations and configurations for a reference sensor will be readily selected by the person of ordinary skill in the art, given the benefit of this disclosure.

In certain embodiments, the exact position of the connection of the leads or interconnects to the reference sensor is not critical. In particular, thermal averaging of the temperature of the sensor reduces errors or aberrations that may occur from sensor to sensor due to the differences in position of the reference sensor relative to the position of the sample support or the position of the sensor in the furnace. In some examples, the interconnects may be connected on substantially the same side of the reference sensor, whereas in other examples the leads may be connected on opposite sides of the reference sensor to provide physical support. The first lead placement, relative to placement of the second lead, is not critical so long as the leads do not electrically interfere with each other during operation of the reference sensor. Similarly, placement of the leads for the reference sensor, relative to placement of the leads or interconnects for the sample support, is not critical so long as the leads do not electrically interfere in such a way to provide unwanted interference with the thermal analysis measurements.

In some examples, each of the interconnects or leads and the reference sensor may be made from numerous materials, such as those materials listed above for the sample support. Desirable features of a material for use as a reference sensor include, but are not limited to, the material does not undergo undesirable thermal events over the desired operating temperature range, the material is generally inert or unreactive toward the sample or the thermocouple, and the thermal conductivity and heat capacity of the reference are desirably similar to those of the sample. In certain embodiments, the leads and reference sensor may each independently be, or include, platinum, rhodium, rhenium, palladium, iridium, tungsten, gold, copper, silver, alumina, zirconia, yttria and mixtures of these illustrative materials. In some examples, the materials used in the interconnects are selected such that a thermocouple having a desired response or temperature range is provided. In certain embodiments, the length of the leads or interconnects that are coupled to the reference sensor may vary from about 70 mm to about 100 mm, more particularly, about 75 mm to about 90 mm, for example, about 80 mm. In certain examples, the thickness of the interconnects may vary from about 0.1 mm to about 0.3 mm, more particularly about 0.15 mm to about 0.25 mm, for example, about 0.2 mm. In some examples, the sample support and reference sensor may all be produced using the same material or materials such that the thermal properties of the components generally match each other.

In certain examples, the support member 120 (FIG. 1) may take the form of a rod or tube that can provide physical support to the sample support and/or the reference sensor. In certain embodiments, the support member may be produced using materials that match the thermal properties of the reference sensor and/or sample support, whereas in other examples, the support member may be made of, or include, materials that differ from those found in the sample support and/or the reference sensor. The support member 120 may be about 55 mm to about 95 mm long, for example, about 75 mm long. The exact length of the support member may vary and the support member may be desirably long enough such that thermal decoupling from the heating element of the furnace is achieved to avoid unwanted thermal gradients, but not so long as to unnecessarily increase the overall size of the furnace needed to house the sensor. The cross-sectional shape of the support member may also vary and in some examples may be circular, ovoid, rectangular, triangular or other suitable geometric shapes. Illustrative materials for use in a support member include, but are not limited to, platinum, rhodium, rhenium, palladium, iridium, tungsten, gold, copper, silver, alumina, zirconia, yttria and mixtures of these illustrative materials.

In certain embodiments, the support member may include two or more longitudinal channels that act as a passageway for the electrical leads or interconnects used to provide signals from the sample support and the reference sensor to a controller or other device. In some examples, each wire may be positioned within its own channel such that electrical cross-talk may be reduced. The longitudinal channels may be placed anywhere within the support member body and may be sized and arranged such that the wire or lead passes from one end of the support member to the other end. Illustrative channel placements are shown in FIGS. 8A, 8B and 8C, where channels 810, 820 and 830 are shown in support members 805, 815 and 825, respectively. The particular cross-sectional shape of the channels is not critical and any shape may be used. In some examples, for ease of production, it may be desirable to use a hollow rod with a single channel that provides for passage of all the interconnects for the sample sensor and the reference sensor through the single channel. In such embodiments, it may be desirable to insulate each of the wires such that electrical cross-talk is reduced. Suitable insulators such as, for example, glass, fibers, non-conductive oxides, ceramics, and other non-conductive substances may be used.

In accordance with certain examples, the electrical interconnects or wires that are used with the reference and sample sensor may be configured to provide the two sides of a hot junction temperature measurement thermocouple. In particular, one of two interconnects may be configured as a platinum/10% rhodium wire and the other may be configured as a platinum wire such that a Type S thermocouple is provided. A similar arrangement may be used to provide a thermocouple for use with the reference sensor. In operation, the temperature difference in the wires can cause a voltage difference that results in flow of a current (the Seebeck effect). In some examples, the thermocouple coupled to the sample support is of the same type as the thermocouple coupled used in the reference sensor. Illustrative thermocouple types include, but are not limited to, Type B (Platinum/30% Rhodium (+) versus Platinum/6% Rhodium (−)), Type E (Nickel/10% Chromium (+) versus constantan (−)), Type J (Iron (+) versus constantan (−)), Type K (Nickel/10% Chromium (+) versus Nickel/5% Aluminum-Silicon (−)), Type R (Platinum/13% Rhodium (+) versus Platinum (−), and Type S (Platinum/10% Rhodium (+) versus Platinum (−)), as described, for example, in ANSI C96.1-1964. Additional thermocouples such as, for example, pure platinum, platinum palladium, platinum iridium, platinum tungsten and tungsten rhenium thermocouples, however, will be selected by the person of ordinary skill in the art, given the benefit of this disclosure. In particular, any materials that possess predictable output voltages as a function of temperature may be used in the thermocouples.

In some examples, the thermal conductance of the reference sensor may reduce the criticality as to where the exact location the thermocouple hotspot is positioned/welded. The same thermal conductance provides a 'physical averaging' of the temperature alongside the reference sensor, which makes the dependency on accurate positioning of the reference sensor in the center of the furnace less relevant as well. As discussed herein a significant advantage of using a reference sensor cylindrical ring configuration is that the furnace "sees" the sample crucible and the reference ring in a substantially equal way, which equalizes heat flow to both of them, whereas the sample crucible and the reference ring hardly "see" each other. This lack of thermal coupling increases the overall sensitivity of thermal measurements made using the sensors disclosed herein.

In some examples, the thermocouple wires may be coupled to connector 130 (FIG. 1). In some embodiments, each wire may have its own connection to the connector 130 such that four separate connections are made to the connector 130. In other examples, two or more wires may share a common connection to facilitate easier assembly of the sensor. The connector 130 may be used to provide a signal from the sensors such that when the sensor is coupled to a microbalance through the connector 130, signals or data from the thermocouple wires/channels maybe transmitted through support member and/or the microbalance and to systems or sub-systems for analysis or recording thereof. Such systems or sub-systems may include hardware and/or software as described in more detail below.

In accordance with certain examples, the sensors disclosed herein are particularly useful in thermal analysis and simultaneous thermal analysis. Illustrative thermal analysis techniques, which may be performed alone or together with one or more other thermal analysis techniques, include but are not limited to thermogravimetric analysis (TGA), differential thermal analysis (DTA) and differential scanning calorimetry (DSC). In TGA, the mass of a sample is measured as a function of temperature. TGA may be used, for example, to determine water of crystallization, follow degradation of materials, determine reaction kinetics, to study oxidation and reduction, or other applications. During a typical TGA measurement, heat is provided to the sample to force chemical reactions and/or physical changes in materials. TGA provides a quantitative measurement of mass change in materials associated with the reactions, transitions and/or thermal degradation. For example, TGA can measure the change in mass from dehydration, decomposition, and oxidation of a sample with time and temperature. During a TGA measurement, the mass is recorded as a function of time or temperature. The results may be plotted to provide a characteristic thermogravimetric curve for a given specific material or chemical compound due to physicochemical reactions occurring over specific temperature ranges and heating rates. These unique characteristics are related to the molecular structure of the sample.

In certain examples, the sensors disclosed herein may be used in differential thermal analysis (DTA). In DTA, the difference in temperature of the sample and a reference are recorded while both are subjected or exposed to the same thermal environment. Temperature profiles or ramps may be implemented, and the temperature of the sample and reference may be monitored throughout the temperature profile. DTA may be particularly useful where there is no change in mass, either over the entire temperature profile or during some portion of the temperature profile. DTA can provide, for example, whether a transition is endothermic or exothermic. In a typical analysis the difference in the temperature of the sensor ($T_S$) and the reference temperature ($T_R$) may be used to determine thermodynamic properties. For example, $T_S$-$T_R$ as a function of temperature may be used to determine that the change is endothermic (a decrease in the curve at higher temperature) or exothermic (an increase in the curve at higher temperature). DTA is useful in numerous analyses including, but not limited to, sample identification, quantitative composition analysis, phase diagrams, hydration-dehydration, thermal stability, polymerization, purity, and reactivity.

In certain examples, the sensors disclosed herein may be used in differential scanning calorimetry (DSC). DSC is similar to DTA. In heat flux DSC, temperature differences, as required with the DTA (delta temperature) signal, are interpreted to a heat flow (in energy units, mW). This technique can be used as there is a well-defined and reproducible thermal contact, and therefore thermal resistance, in between sample, sample crucible and sample temperature sensor.

Certain embodiments of the sensors disclosed herein are particularly suited for use with thermal analysis systems that can implement two or more thermal analysis techniques. As discussed above, TGA detects thermal events occurring as a result of a mass change, but does not detect a phase change where there is no change in mass, e.g., melting. Melting may be detected using DTA. By implementing both TG analysis and DTA simultaneously on a sample, increased amounts of information may be obtained while total analysis time may be reduced. The amount of sample required may also be reduced, because a single sample is used for both the TG analysis and the DTA analysis rather than having to use two samples for separate analyses. Illustrative simultaneous thermal analysis devices may implement, for example, TG and DTA, DTA and DSC, TG and DSC or even TG, DTA and DSC. Additional simultaneous thermal analysis methods using the sensors disclosed herein will be readily selected by the person of ordinary skill in the art, given the benefit of this disclosure.

Figure 9:
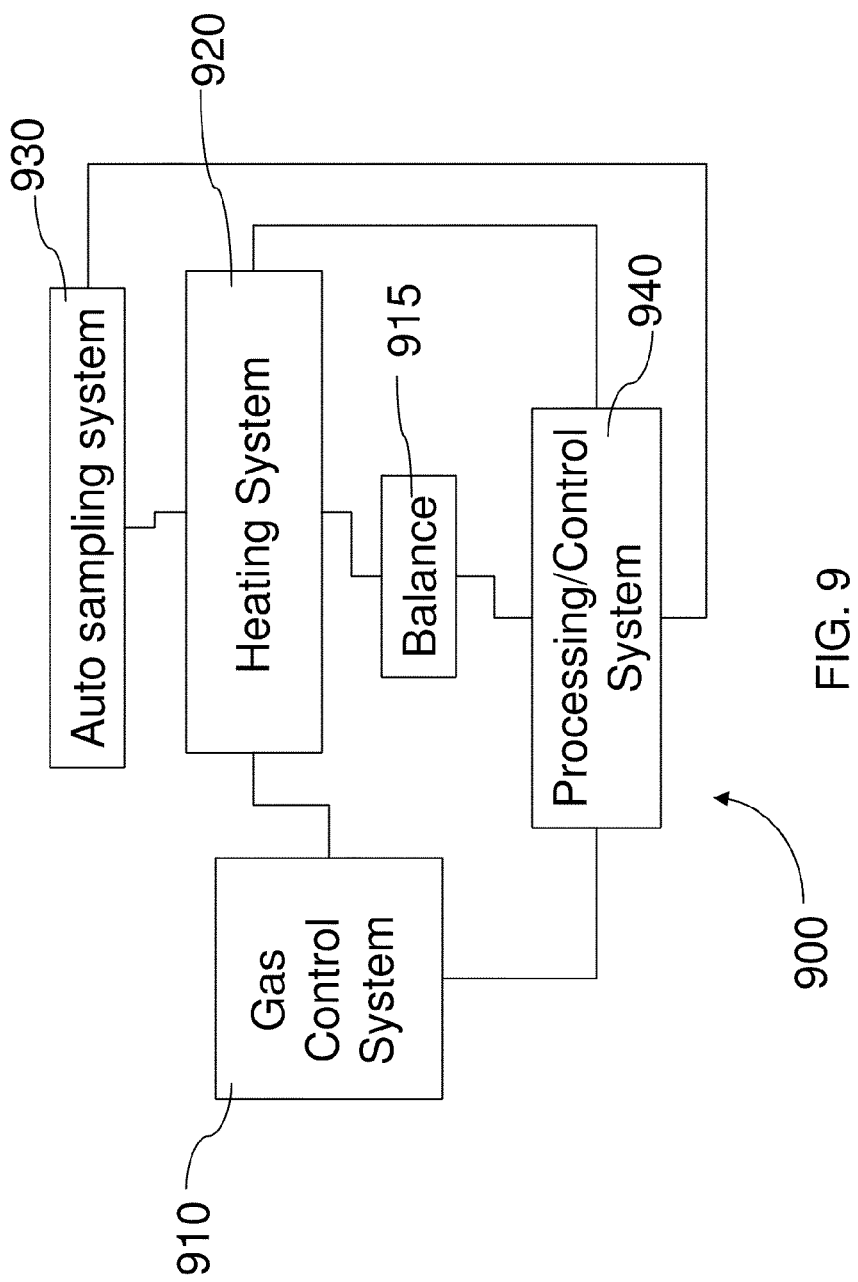
FIG. 9 is a block diagram of a system for thermal analysis, in accordance with certain examples.
Figure 10:
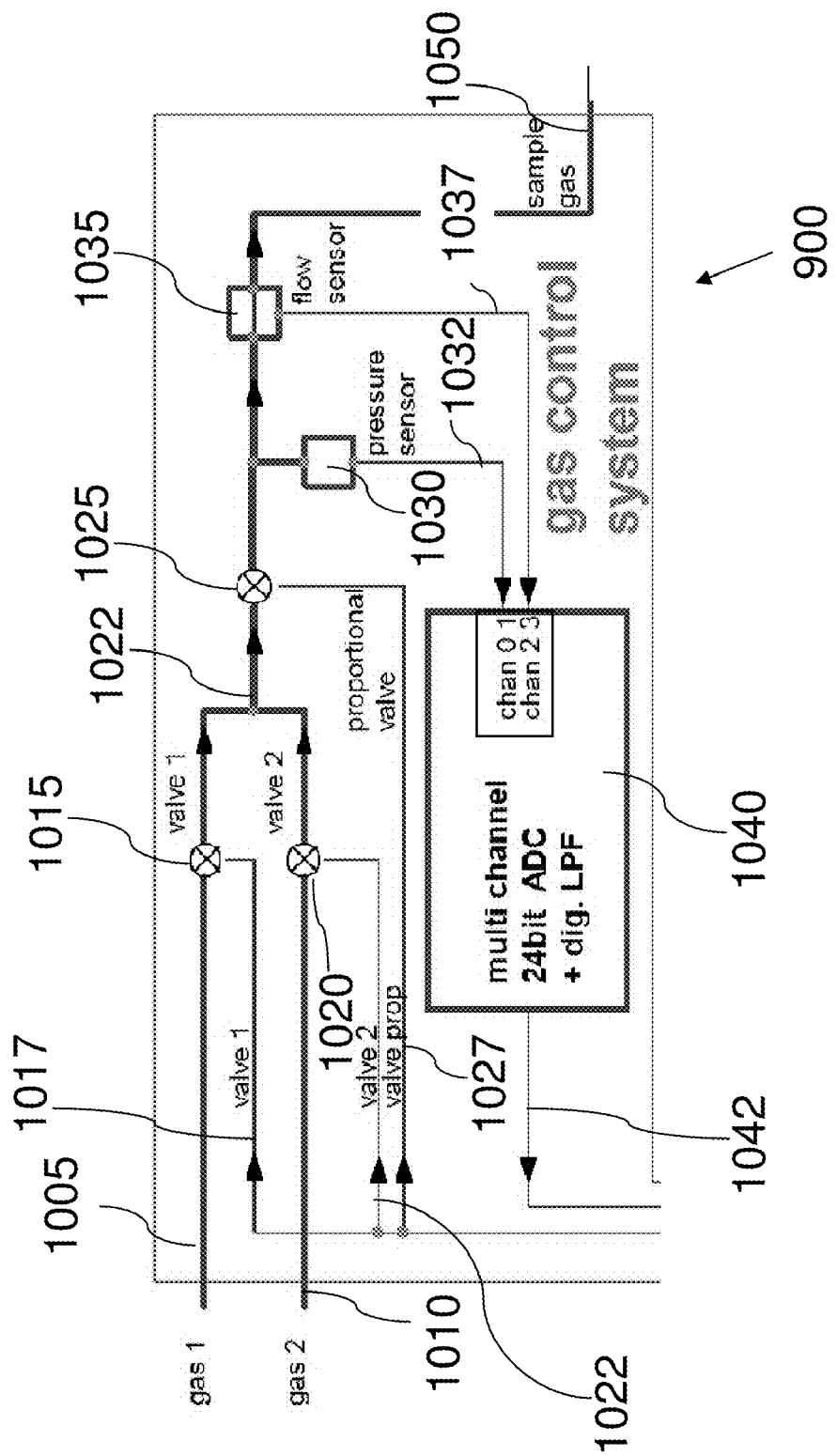
FIG. 10 is a schematic of an illustrative gas control system, in accordance with certain examples.
Figure 11:
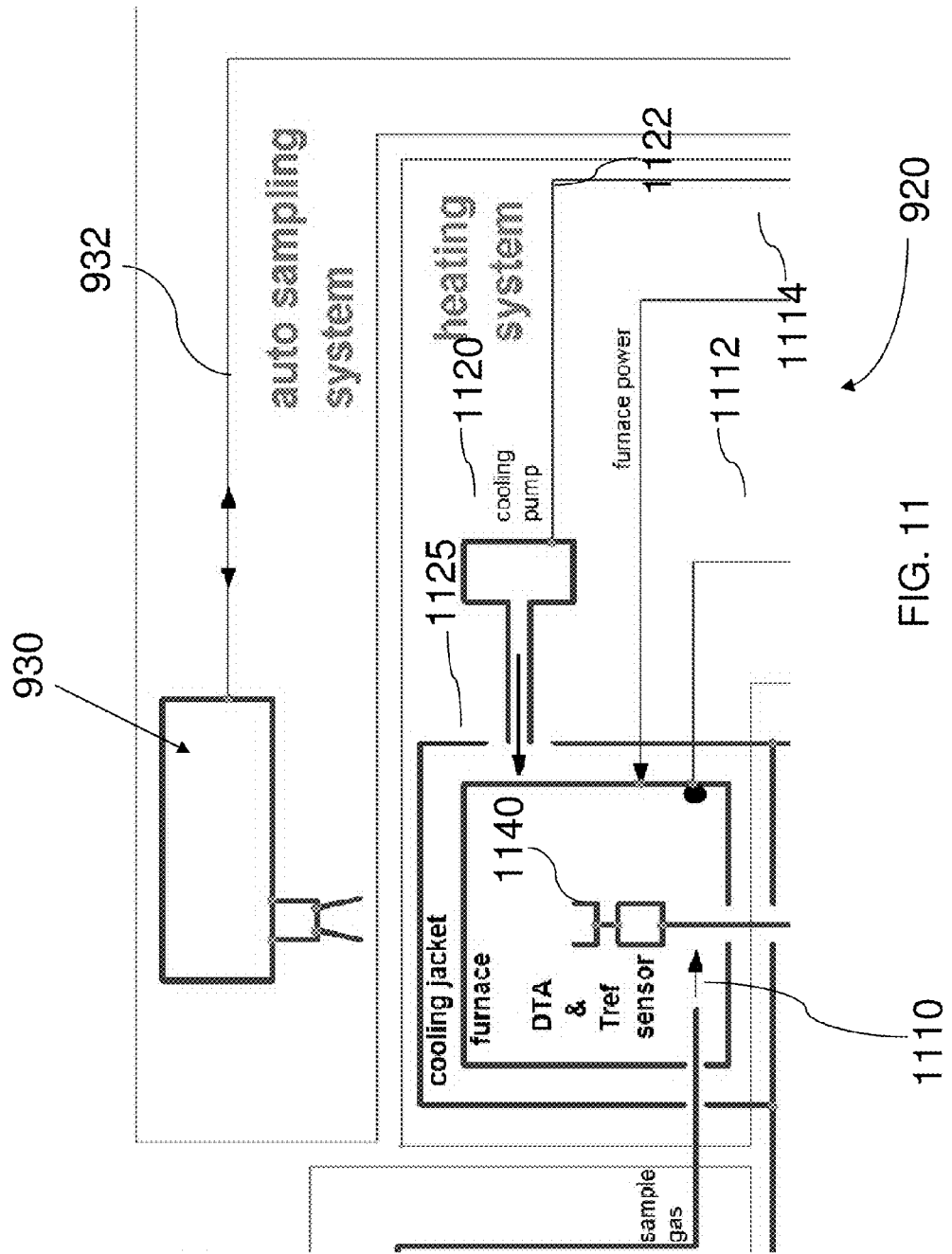
FIG. 11 is a schematic of an illustrative heating system and an illustrative autosampling system, in accordance with certain examples.

In certain examples, a thermal analysis system may include, for example, the components or systems shown in FIG. 9. The system 900 includes a gas control system 910, a balance, 915, a heating system 920, an autosampling system 930 each coupled to a processing/control system 940 The gas control system 900 may include, for example, suitable gases, fluid lines, flow valves, pressure sensors and flow sensors to introduce one or more sample gases into the heating system. An illustration of an embodiment of a gas control system is shown in FIG. 10. The gas control system 900 comprises fluid conduits 1005 and 1010 configured to receive a first and second sample gas, respectively (though in some embodiments only a single sample gas may be used). The fluid conduits 1005 and 1010 are each coupled to valves 1015 and 1020, respectively, which are controlled by the processing/control system 940 through leads 1017 and 1022, respectively. A proportional valve 1025 is also coupled to the fluid conduits 1005 and 1010 through a fluid conduit 1022. The proportional valve 1025 is also controlled by the processing/control system 940 through lead 1027. A pressure sensor 1030 and a flow sensor 1035 are each coupled to a fluid conduit to provide feedback to the processing/control system 940 by sending signals through leads 1032 and 1037, respectively, to analog-to-digital converter 1040, which passes the signal to the processing/control system through lead 1042. The pressure sensor 1030 and the flow sensor 1035 provide signals regarding gas flow through the gas control system 910. The sample gas flow is provided to the heating system 920 through a fluid conduit 1050. In some examples, the gas control system 900 may be used to provide gas from one or the other gas source but not both, whereas in other examples, the gases may be mixed prior to introduction to the heating system 920. Gas flow rates may vary depending on the selected thermal analysis method and illustrative gas flow rates include, but are not limited to, 0 mL/minute to about 100 mL/minute, more particularly about 5 mL/minute to about 100 mL/minute. Various devices and fittings such as, for example, Swagelock-type fittings may be used to couple the gases and gas flow lines to the heating system 920. Referring now to FIG. 11, an illustrative heating system and autosampling system is shown. The heating system 920 includes a furnace 1110 that receives cooling gas from the gas control system 910. The furnace also include a cooling pump 1120 that is operative to provide chilled water or fluid to a cooling jacket 1125 to cool the oven to a desired temperature before or after a measurement. Furnace power is provided through a lead 1114 from the processing/control system or through a separate controller or power supply. The temperature inside the furnace 1110 is sensed using, for example, a thermocouple, and the signals may be sent to the control system through a lead 1112 such that the temperature may be adjusted or controlled during a measurement. The cooling pump 1120 may be controlled by the processing/control system through a lead 1122. In some examples, the furnace may be a top-loading furnace such that loading and unloading in manual and automated modes is simplified. Illustrative shapes and dimensions for suitable furnaces include, but are not limited to, furnaces generally cylindrical and having an inner diameter of about 10 mm to about 15 mm, for example about 13 mm, an outer diameter of about 18 mm to about 22 mm, for example about 20 mm, and an overall height of about 20 mm to about 30 mm, for example about 25 mm. In some examples, the overall size of the furnace is minimized, based on the size of the sensor, such that the overall footprint of the furnace is reduced. The furnace may be fluidically coupled to a cooling source such as air, water or some other cooling fluid. Such cooling fluid may be circulated through, for example, a jacket around the outer surfaces of the furnace such that rapid heat transfer is facilitated to cool the oven. In addition, the furnace may include one or more exhaust fans to rapidly exhaust hot air and/or exchange the furnace air with cooler ambient air.

Referring now to the autosampling system 930, the autosampling system 930 may comprise one or more sample reservoirs to receive a plurality of samples. The plurality of samples may be a plurality of crucibles each containing a sample. The autosampling system 930 may include one or more robotic arms or gantries to load a sample into the sensor 1140 for analysis. Subsequent to analysis, the autosampling system may remove the crucible and sample and insert a new crucible and sample on the sensor 1140. Illustrative autosampling systems include those commercially available from PerkinElmer Life and Analytical Sciences, Inc. such as, for example, those available for use with, or in, a Jade-DSC or STA 6000 instrument. The autosampler may be controlled, for example, through a lead 932 that connects the processing/control system to the autosampling system 930. In some examples, the autosampling system 930 may be used to load a sample, and after a specified or desired time, remove the sample and load a new sample. The rate at which sample is loaded may vary with the type and nature of the thermal analysis being performed. In certain embodiments, the autosampling system may be configured to load a new sample about every 60 minutes or less, for example about every 8 minutes or less than or equal to 5 minutes.

Figure 12:
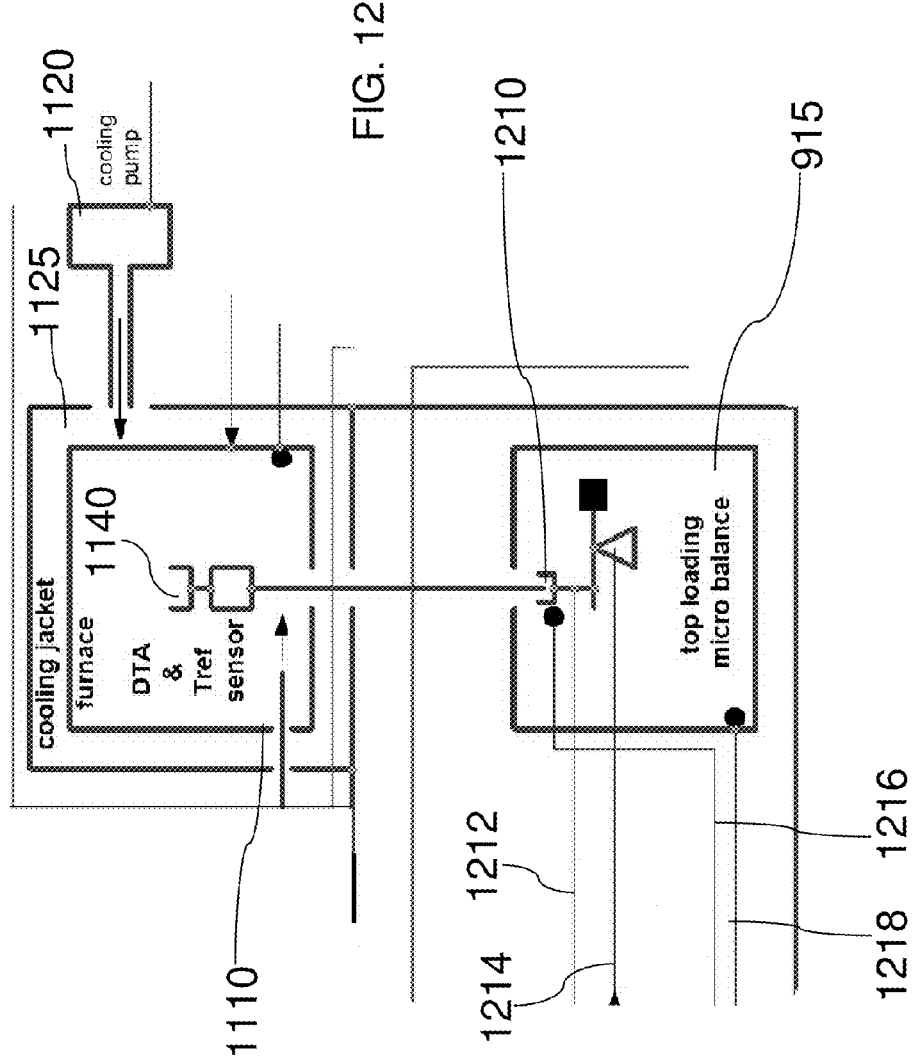
FIG. 12 is a schematic of an illustrative balance coupled to a heating system, in accordance with certain examples.

In some examples, the thermal analysis system may also include a balance 915. One illustration of a balance 915 coupled to a sensor as described herein is shown in FIG. 12. The sensor 1140 may be coupled to the balance 915 through a connector 1210. The balance 915 may be located external to the heating system or some portion of the balance may be inside the heating system.

In operation, signals from various components may be sent through electrical connections or paths to other components of the system. For example, the signal from the sample sensor and the reference sensor thermocouples may be sent to the processing/control system through a path or connection 1212. The balance itself may be controlled by sending signals by a connection 1214. The signal of the cold junction of the reference sensor, which may be, for example, a NTC (negative temperature coefficient) signal, may be sent to the processing/control system through a connection 1216, and, the NTC signal of the microbalance may be sent to the processing/control system through a connection 1218. While the connections shown in the figures may be represented as a single line or pathway, the actual connection used may include two or more connections or pathways such that a desired signal or measurement may be received and/or sent. Suitable microbalances include, but are not limited to, those that include, or can receive, one or more of a signal cold junction temperature measurement and the feed-through of the sensor signals. The microbalance may be positioned within the heating system or may be external to the heating system, depending on the exact configuration of the thermal analysis system.

Figure 13:
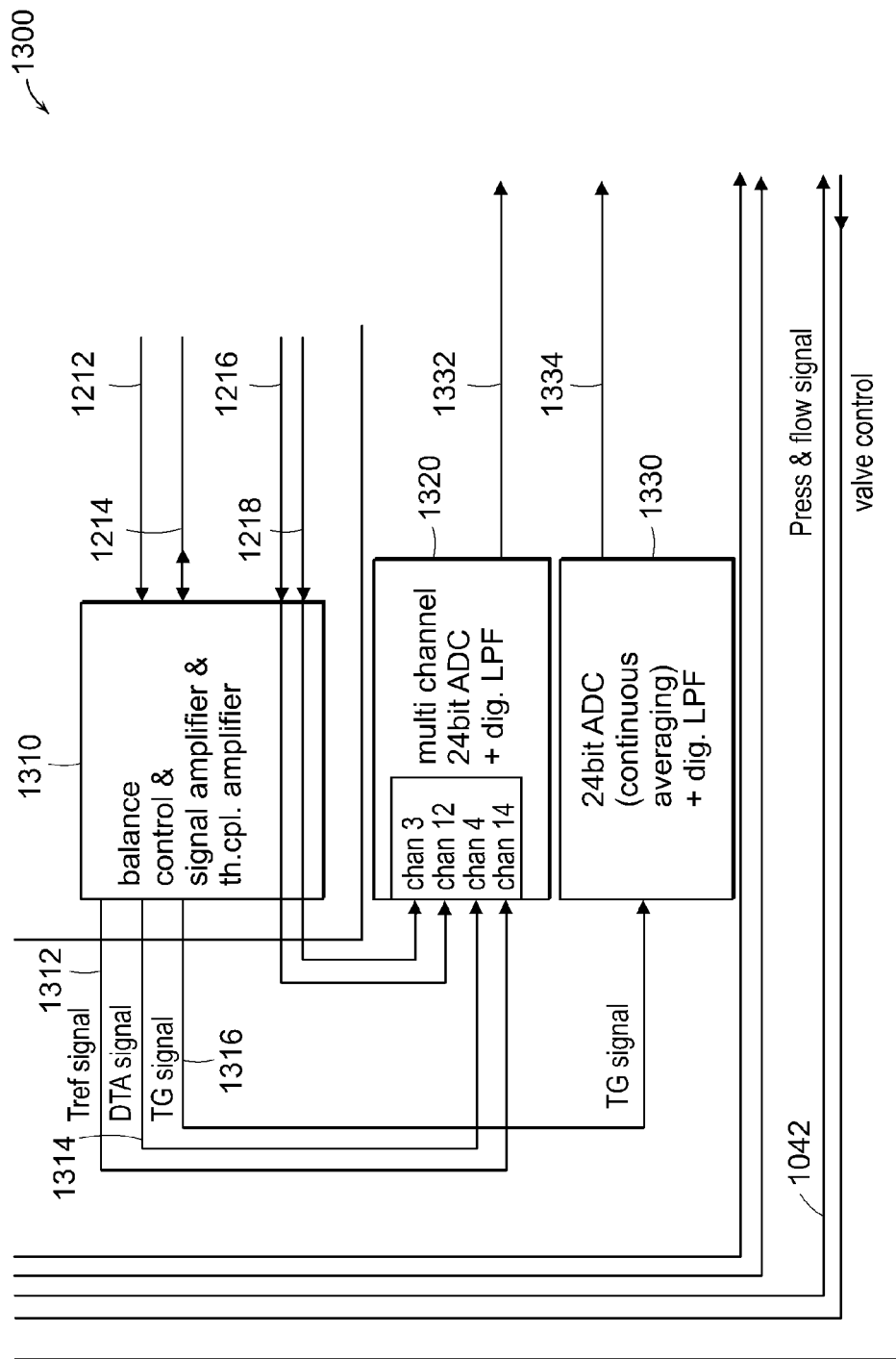
FIG. 13 is a schematic of a sub-system of a control system, in accordance with certain examples.

Referring to FIG. 13, a sub-system of an illustrative processing/control system is shown. The subsystem 1300 comprises a balance control, signal amplifier and thermocouple amplifier 1310. The subsystem 1300 includes a balance control and amplifier component 1310 that is configured to control the balance through a connection 1214. The component 1310 may also configured to receive a signal from the sample sensor and the reference sensor thermocouples through a connection 1212. The component 1310 receives the NTC (negative temperature coefficient) signal of the cold junction of the reference sensor through a connection 1216 and the NTC signal of the microbalance through a connection 1218. These NTC signals may be amplified using the component 1310 and provided to a component 1320. The component 1310 also provides a reference temperature signal through a connection 1312 to the component 1320, which is operative as an analog-to-digital converter (ADC) and a digital low pass filter (LPF). Component 1320 may be, for example, a multi-channel ADC such as a LTC2449 (Linear technology, multi channel 24 bit ADC). In this illustration, the component 1310 also provides a DTA signal through a connection 1314 to the component 1320. A TG signal from the component 1310 is provided through a connection 1316 to a component 1330, which is also operative as an analog-to-digital converter and a digital low pass filter and may be, for example, another high resolution (24 bit) ADC such as a AD7710 (Analog Devices). The component 1320 may output a signal to another subsystem, as shown in FIG. 14, through a connection 1332, and the component 1330 may output a signal to the other subsystem through a connection 1334.

Figure 14:
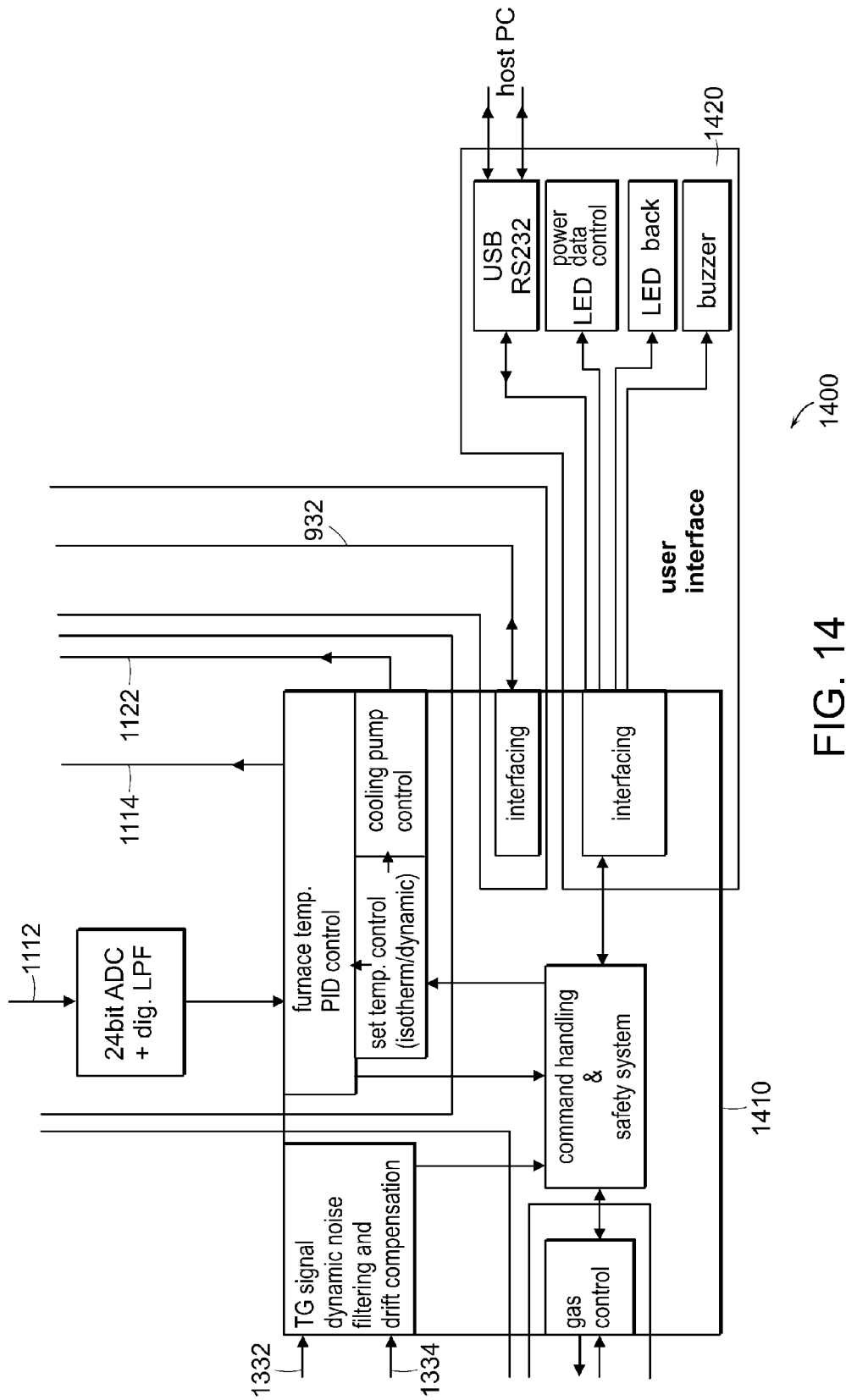
FIG. 14 is a schematic of another sub-system of a control system, in accordance with certain examples.

Referring to FIG. 14, the subsystem 1400 comprises a controller 1410 that is configured to receive and process signals from the subsystem 1310 and other components of the system. The controller 1410 may filter the TG signal, compensate for drift, control the gas flow in the system, control temperature of the furnace through, for example, a proportional-integral-derivative (PID) processor, may control the cooling pump and may output desirable signals or data to a user interface. The subsystem 1410 may also be coupled to one or more interfaces or controllers 1420 such as, for example, a USB interface, one or more LEDs, a switch, a printer, a graphical user interface or the like to provide the user with desired data or parameters for the thermal analysis measurements. Though the embodiment shown in FIGS. 13 and 14 is shown as including subsystems, a single controller or processor may be used to control the thermal analysis system.

In accordance with certain examples, suitable thermal analysis systems that use one or more of the sensors disclosed herein may be operative over a wide mass and temperature range. While the amount of sample used for analysis may vary depending on the thermal properties of the samples, in some instances as little as about 0.5 mg to about 1 mg of sample may be used for an analysis, whereas in some examples, the sample support may be designed to receive 1500 mg or more of sample. The system may implement temperature profiles that range from 15° C. to about 1000° C. at heating rates that may vary, for example, from about 0.1 to 100° C./minute. Temperature measurements may be made and accurate to about 0.5° C. The furnace may be cooled at a rapid rate such as, for example, about 1000° C. to about 100° C. in less than twelve minutes or about 1000° C. to about 30° C. in less than twenty minutes using for example forced air and/or a chiller. As discussed further below, the systems may also be coupled to one or more additional devices to provide a hyphenated or conjugated system that can perform simultaneous thermal analysis as well as one or more other analytical techniques.

In some examples, one or more other analytical devices may be conjugated to the thermal analysis system for additional analysis of the materials being analyzed or for analysis of gases evolved during the thermal analysis. Illustrative analytical devices include, but are not limited to, a mass spectrometer (MS), an infrared (IR) spectrometer, a gas chromatograph (GC) and combinations of these techniques. Block diagrams illustrating some hyphenated devices are shown in FIGS. 15A-15D. Such hyphenated devices may be particular useful for evolved gas analysis, where one or more gases is evolved from the sample during a thermal analysis measurement. Such gases may be directed or drawn into another instrument or device using suitable devices such as, for example, vacuum pumps, fans, head space sampling and the like. In some examples, a heated tube provides fluid communication between the thermal analysis devices and the MS such that species that evolve as gases in the thermal analysis device may be kept as gases during the transfer to the MS. Additional suitable devices and methods for transferring species from a thermal analysis device to a MS will be readily selected by the person of ordinary skill in the art, given the benefit of this disclosure.

Referring to FIG. 15A, a system 1500 may comprise a device for simultaneous thermal analysis 1510, or in certain instances a device configured for a single type of thermal analysis, coupled to a mass spectrometer 1515. The STA device 1510 may be configured to perform any two or more thermal analysis methods described herein or other thermal analysis methods that may be implemented using the sensors described herein. The mass spectrometer 1515 may be any mass spectrometer commonly used in chemical analysis such as those commercially available, for example, from PerkinElmer Life and Analytical Sciences, Inc. (Waltham, Mass.). Illustrative mass spectrometers include, but are not limited to, those configured to use or implement a magnetic sector mass analyzer, a quadrupole mass analyzer, an ion trap analyzer, a time-of-flight analyzer, those implementing electrospray deionization and other suitable mass analyzers that may separate species with different mass-to-charge ratios. It may be desirable to include one or more valves, fittings or devices to compensate for the difference in pressure between the STA device 1510 and the mass spectrometer 1515. Such pressure compensation will be achieved by the person of ordinary skill in the art, given the benefit of this disclosure.

Referring to FIG. 15B, a system 1520 may comprise a device for simultaneous thermal analysis 1525, or in certain instances a device configured for a single type of thermal analysis, coupled to an infrared (IR) spectrometer 1530. The STA device 1525 may be configured to perform any two or more thermal analysis methods described herein or other thermal analysis methods that may be implemented using the sensors described herein. The infrared spectrometer may be any commonly used infrared spectrometers such as, for example, continuous wave infrared spectrometers, single or dual beam infrared spectrometers, or interference spectrometers such as a Fourier transform infrared spectrometer. Suitable other infrared spectrometers and suitable methods for coupling a STA device to an IR device will be recognized by the person of ordinary skill in the art, given the benefit of this disclosure.

Referring to FIG. 15C, a system 1540 may comprise a device for simultaneous thermal analysis 1545, or in certain instances a device configured for a single type of thermal analysis, coupled to a gas chromatograph (GC) 1550. The STA device 1545 may be configured to perform any two or more thermal analysis methods described herein or other thermal analysis methods that may be implemented using the sensors described herein. The GC 1550 may receive evolved gas from the STA device 1545 and separate species within the evolved gas. For example, it may be desirable to separate gaseous reaction products evolved during the thermal analysis. It will be within the ability of the person of ordinary skill in the art, given the benefit of this disclosure, to select suitable GC devices for use with an STA device.

Referring to FIG. 15D, a system 1560 may comprise a device for simultaneous thermal analysis 1565, or in certain instances a device configured for a single type of thermal analysis, coupled to a gas chromatograph 1570 which itself is coupled to a mass spectrometer 1575. The STA device 1565 may be configured to perform any two or more thermal analysis methods described herein or other thermal analysis methods that may be implemented using the sensors described herein. The GC 1570 and the MS 1575 may each be, for example, any of the illustrative GC and MS devices discussed in reference to FIGS. 15A and 15C or other suitable GC and MS devices. The illustrative systems shown in FIGS. 15A-15D may also include additional components such as, for example, autosamplers, filters, analysis systems and software, computer interfaces and the like.

In accordance with certain examples, the devices and systems disclosed herein may be controlled or used with at least in part, a computer system. The computer systems may be, for example, general-purpose computers such as those based on Unix, Intel PENTIUM-type processor, Motorola PowerPC, Sun UltraSPARC, Hewlett-Packard PA-RISC processors, or any other type of processor. It should be appreciated that one or more of any type computer system may be used according to various embodiments of the technology. Further, the system may be located on a single computer or may be distributed among a plurality of computers attached by a communications network. A general-purpose computer system according to one embodiment may be configured to perform any of the described functions including but not limited to: data acquisition, autosampler control, furnace temperature control, data logging, data analysis and the like. It should be appreciated that the system may perform other functions, including network communication, and the technology is not limited to having any particular function or set of functions.

For example, various aspects may be implemented as specialized software executing in a general-purpose computer system. The computer system may include a processor connected to one or more memory devices, such as a disk drive, memory, or other device for storing data. The memory is typically used for storing programs and data during operation of the computer system. Components of computer system may be coupled by an interconnection mechanism, which may include one or more busses (e.g., between components that are integrated within a same machine) and/or a network (e.g., between components that reside on separate discrete machines). The interconnection mechanism enables communications (e.g., data, instructions) to be exchanged between system components. The computer system typically is electrically coupled to an interface on the STA device, and/or additional devices in the case of hyphenated systems, such that electrical signals may be provided from the STA device to the computer system for storage and/or processing.

Computer system may also include one or more input devices, for example, a keyboard, mouse, trackball, microphone, touch screen, and one or more output devices, for example, a printing device, status or other LEDs, display screen, speaker. In addition, computer system may contain one or more interfaces that connect computer system to a communication network (in addition or as an alternative to the interconnection mechanism). The storage system of the computer typically includes a computer readable and writeable nonvolatile recording medium in which signals are stored that define a program to be executed by the processor or information stored on or in the medium to be processed by the program. For example, the temperature profile used in certain embodiments disclosed herein may be stored on the medium. The medium may, for example, be a disk or flash memory. Typically, in operation, the processor causes data to be read from the nonvolatile recording medium into another memory that allows for faster access to the information by the processor than does the medium. This memory is typically a volatile, random access memory such as a dynamic random access memory (DRAM) or static memory (SRAM). It may be located in storage system, as shown, or in memory system. The processor generally manipulates the data within the integrated circuit memory and then copies the data to the medium after processing is completed. A variety of mechanisms are known for managing data movement between the medium and the integrated circuit memory element, and the technology is not limited thereto. The technology is not limited to a particular memory system or storage system.

The computer system may also include specially-programmed, special-purpose hardware, for example, an application-specific integrated circuit (ASIC). Aspects of the technology may be implemented in software, hardware or firmware, or any combination thereof. Further, such methods, acts, systems, system elements and components thereof may be implemented as part of the computer system described above or as an independent component.

In some examples, the computer system may be a general-purpose computer system that is programmable using a high-level computer programming language. The computer system may be also implemented using specially programmed, special purpose hardware. In the computer system, the processor is typically a commercially available processor such as the well-known Pentium class processor available from the Intel Corporation. Many other processors are available. Such a processor usually executes an operating system which may be, for example, the Windows 95, Windows 98, Windows NT, Windows 2000 (Windows ME), Windows XP or Windows Vista operating systems available from the Microsoft Corporation, MAC OS System X operating system available from Apple Computer, the Solaris operating system available from Sun Microsystems, or UNIX or Linux operating systems available from various sources. Many other operating systems may be used. In addition or alternative to a processor, the computer system may include a controller such as for example and 8-bit or 16-bit controller such as SAB-C517A (commercially available from Infineon) or ST10C269 (commercially available from ST-Microelectronics), respectively. Other controllers such as 32-bit or higher controllers may also be used in place of a processor or in addition to the processor of the computer system.

The processor and operating system together define a computer platform for which application programs in high-level programming languages are written. It should be understood that the technology is not limited to a particular computer system platform, processor, operating system, or network. Also, it should be apparent to those skilled in the art that the present technology is not limited to a specific programming language or computer system. Further, it should be appreciated that other appropriate programming languages and other appropriate computer systems could also be used.

In certain examples, the hardware or software is configured to implement cognitive architecture, neural networks or other suitable implementations. For example, a database of known temperature profiles may be linked to the system to provide access to known thermal properties for a class of substances. Such configuration would allow for storage and access of a large number of materials whose thermal properties are known, which can increase the functionality of the devices and systems disclosed herein.

One or more portions of the computer system may be distributed across one or more computer systems coupled to a communications network. These computer systems also may be general-purpose computer systems. For example, various aspects may be distributed among one or more computer systems configured to provide a service (e.g., servers) to one or more client computers, or to perform an overall task as part of a distributed system. For example, various aspects may be performed on a client-server or multi-tier system that includes components distributed among one or more server systems that perform various functions according to various embodiments. These components may be executable, intermediate (e.g., IL) or interpreted (e.g., Java) code which communicate over a communication network (e.g., the Internet) using a communication protocol (e.g., TCP/IP). It should also be appreciated that the technology is not limited to executing on any particular system or group of systems. Also, it should be appreciated that the technology is not limited to any particular distributed architecture, network, or communication protocol.

Various embodiments may be programmed using an object-oriented programming language, such as SmallTalk, Basic, Java, C++, Ada, or C# (C-Sharp). Other object-oriented programming languages may also be used. Alternatively, functional, scripting, and/or logical programming languages may be used. Various aspects may be implemented in a non-programmed environment (e.g., documents created in HTML, XML or other format that, when viewed in a window of a browser program, render aspects of a graphical-user interface (GUI) or perform other functions). Various aspects may be implemented as programmed or non-programmed elements, or any combination thereof.

In certain examples, a user interface may be provided such that a user may enter desired start and stop temperatures, heating rate, autosampling rate and the like. Other features for inclusion in a user interface will be readily selected by the person of ordinary skill in the art, given the benefit of this disclosure. In some examples, the user interface may be one such as the one commonly found on Pyris software commercially available from PerkinElmer, Inc. Other suitable software interfaces may also be used depending on the intended use of the STA device and any devices to which it is coupled.

In some examples, the illustrative computer systems, or components thereof, described above may be implemented to control all the features of a STA device by integrating suitable components on a single printed circuit board. In other examples, there may be separate circuit boards for the gas control system, balance controller and signal amplifiers which may be coupled to another circuit board such as, for example, a "main" printed circuit board.

Certain specific examples are described in more detail below to illustrate further some embodiments of the technology disclosed herein.

EXAMPLE 1

Figure 16B:
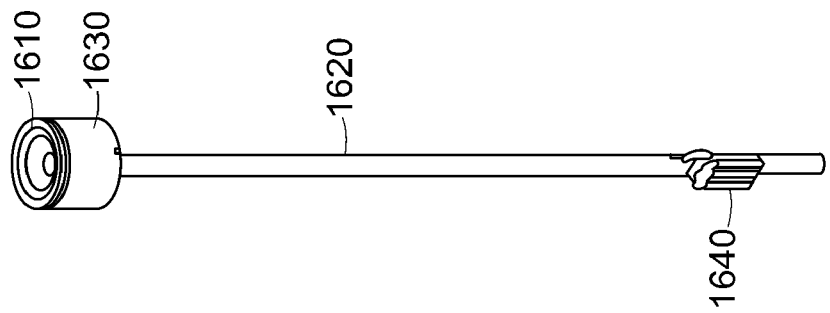
FIGS. 16A and 16B are perspective view of an assembled sensor, in accordance with certain examples.
Figure 16A:
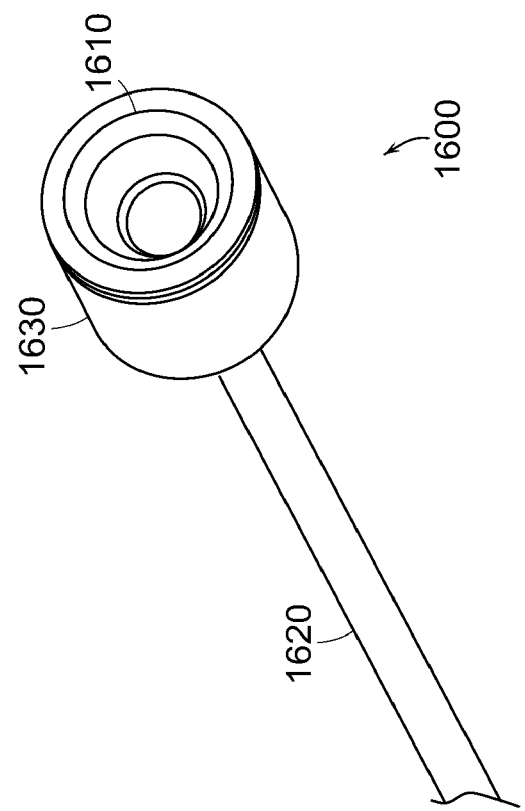
Figure 17D:
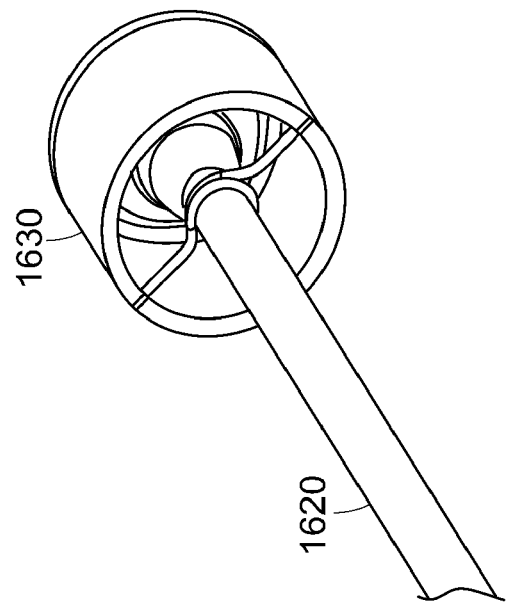
FIGS. 17C and 17D are perspective views showing the bottom of a sensor, in accordance with certain examples.
Figure 17C:
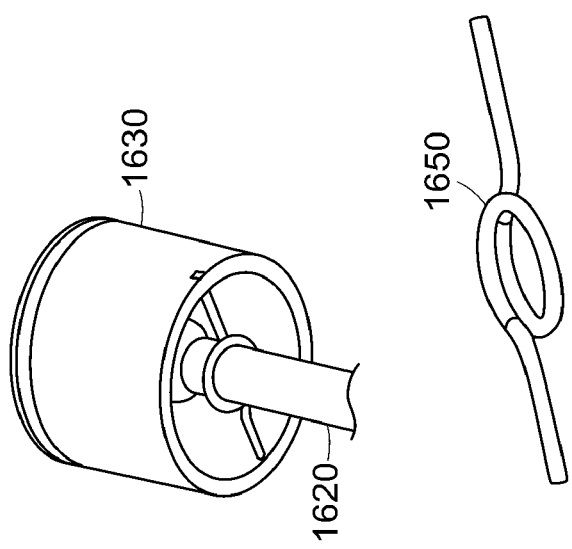

A sensor was produced as follows and as shown in FIGS. 16A-17D. Referring to FIGS. 16A and 16B, the sensor 1600 comprised a sample support 1610 coupled to a support member 1620. A reference sensor 1630 was also coupled to the support member 1620. The support member 1620 included a balance connector 1640 for connecting the sensor 1600 to a microbalance (not shown).

The sensor 1600 was assembled as follows with the component parts referred to below being shown in FIGS. 17A-17D. An alumina (Alsint) support member 1620 with an outer diameter of 1.6 mm and 4 inner channels of 0.3 mm diameter was used. This material was purchased (from Gimex) with a slight oversize (size-tolerances are 'large' for this material), and then centerless polished down to an outer diameter of 1.59 mm +/−0.03 mm. This tight tolerance on outer diameter was used to provide for the exact positioning and repositioning in the furnace. The location of the sensor and sample crucible in the furnace may have a strong effect on the baseline and position accuracy within a few tens of a mm is desirable for use with autosamplers.

Before further machining, the support member 1620 was checked for 'straightness' using a cylindrical clam in a lathe. No larger 'deviations' from the ideal heart line then 0.2 mm were found over a length of 75 mm.

With some diamond cutting tools, the support member 1620 was then machined, and a 'flat' surface was made, opening the underlying channel, where the contact plate will be mounted. On top of that flat surface, two small holes were cut out (0.3×0.5 mm), where the platinum wires will exit the support member channels to be fixed to the two side contacts of the contact plate. On the bottom side, a grove was made to feed through the platinum rhodium wire from the backside channel to the front-side channel. This wire formed one of the two thermocouple-wires for the crucible support and also acted as a pulling wire to remove parts of the sensor if the stem accidentally should crack.

On top of the support member 1620, 4 cuts were made—two of 0.25 mm wide, 0.8 mm deep for the wires feeding to the reference sensor (these wires do not make electrical contact to the sample support 1610, which explains why these cuts were deeper), and two cuts of 0.25 mm wide and 0.4 mm deep for the wires to the sample support 1610.

Manufacturing of the support member 1620 may be performed both manually, with use of a number of guidance tools to obtain the required precision, but as an alternative it can be machined on a CNC-machine. On that CNC-machine, the support member 1620 may be optically lined out on the positions of the four feed through holes, but this is done independently on the lower and the higher side of the stem. Due to the manufacturing process of the support member (extrusion), there is a possibility that the four channels rotate for a number of degrees over the length (75 mm) of the support member 1620. If the support member 1620 was lined up in the machine with, for example, the positions of the channels at only the bottom, there would be the possibility that the cuts on the top side are not correctly made.

In the machined support member 1620, the four wires (two pure platinum, two 90% Platinum, 10% Rhodium) were manually fed through (some precision work done under a stereo microscope). The two platinum wires were fed through the two holes just above the contact plate. The Pt-10% Rh wire on the rear side (to be welded on the crucible support) goes to the bottom of the stem and is fed back via a U-turn to the contact plate (see FIG. 17A). The Pt-10% Rh-wire on the front side is somewhat thicker (0.25 mm) as it provides mechanical support to the reference sensor 1630.

Next, the reference sensor 1630 was pre-assembled. The ring was purchased from Hereaus (Germany), and all Pt and Pt/10% Rh wires were purchased from Chempur. On the bottom of the reference ring, a preformed 0.25 mm Pt-10% Rh support wire was welded using laser welding ($CO_2$-gas laser, laser voltage about 500V, laser pulse duration (single pulse) about 5 milliseconds). The reference ring with support wire 1650 was placed over the support member 1620 before the sample support 1610 was mounted.

The sample support 1610, made of pure platinum (manufacturer Hereaus (Germany)) was mounted/positioned on top of the support member 1620. The two wires to be welded to the sample support 1610 directly contacted the outside of the sample support 1620, and the wires to the reference sensor 1630 were bent back lower (see FIG. 17A).

After positioning the sample support, the assembly was placed in a fixation tool, and a ceramic kit (Ceramabond 503VFG, Aremco) was applied outside the sample support 1610 and on the bottom on the inside (see FIG. 17B). After the ceramic kit was applied, the assembly was hardened in an furnace by heating up to 400° C. The two wires for the sample support were laser welded to that support, the wires towards the reference ring were pre-bent, and the reference ring was positioned and welded to those wires. Next, the reference ring was positioned, and the support wire 1650 on the bottom side was secured with an $Al_2O_3$ Ceramabond kit (see FIG. 17C), followed by a second burn in stage in the electrical furnace.

Finally, the connector plate 1640 was mounted to the support member 1620. This process was performed using a cyanoacrylate-glue (so called: 'super-glue'). The wires to the connector plate 1640 were first bent into position. The positioning was checked for height, alignment and mounting depth. After soldering all wires and cleaning the contact plate, each sensor was color marked, and a final burn run up to 1000° C. was performed, together with a functional test and a DTA baseline recording.

The final dimensions of the sensor (see FIGS. 16A-17D) were as follows: a 78 mm long support member 1620 having an inner diameter of 1.6 mm and an outer diameter of 2.4 mm; a cylindrical reference ring sensor 1630 have a length of 5 mm, an outer diameter of 7 mm and an inner diameter of 6 mm; a 6 mm long balance connector 1640 located 7 mm from the bottom of the support member 1620; and a circular sample support 1610 with an outer surface located 0.25 mm from an inner surface of the reference sensor 1630.

EXAMPLE 2

To properly construct and dimension a reference sensor, the thermal properties of the reference sensor may be matched to those of the sample support and/or a crucible containing the sample such that the furnace "sees" the reference sensor and the crucible similarly. For example, to design a reference sensor for a crucible that is used in an existing Pyris6 TGA device, a platinum reference sensor having a desired mass and shape may be used.

The following calculations were performed to assess the properties of the reference sensor for a particular dimension and material. A crucible size of diameter of 7 mm, a height of 5 mm, a weight of 175 mg, and a material of aluminum oxide was used. Outside surface area of the crucible was (Pi*7*5) =110 $mm^2$. The heat capacitance was 0.154 J/K, the specific heat of $Al_2O_3$ times the crucible weight.

To get the same heat capacity for the platinum reference ring, about 1.17 g may be used. For the same surface, the reference ring may have a diameter of 7 mm and the same height as the crucible, so 5 mm. The thickness of the platinum reference ring is then taken to be 0.5 mm, which results in the required weight of 1.17 g. The physical properties of alumina and platinum are as follows: alumina has a specific weight of 3.89 kg/Liter and a specific heat of 880 J/kg-K; platinum has a specific weight of 21.4 kg/Liter and a specific heat of 130 J/kg-K.

The results of the calculations are shown in Tables I (for the crucibles) and II (for the reference sensors) below. The "Seiko low" and "Seiko high" crucibles are the ones used in a Diamond7 series, and were included in these calculations for alternative figures and crucible materials

TABLE I

| Crucible | Mass (mg) | Height (cm) | Diameter (cm) | Surface area (mm$^2$) | Heat Capacity (J/K) |
|---|---|---|---|---|---|
| TGA | 175 | 5 | 7 | 109.95 | 0.154 |
| Seiko low | 89 | 2.5 | 5.2 | 40.84 | 0.078 |
| Seiko high | 167 | 5 | 5.2 | 81.69 | 0.147 |

TABLE II

| Length (cm) | Height (cm) | Thickness (cm) | Mass (mg) | Heat Capacity (J/K) | Ring Diameter (cm) | Surface (mm$^2$) |
|---|---|---|---|---|---|---|
| 25 | 5 | 0.5 | 1337.5 | 0.174 | 7.96 | 125 |
| 22 | 5 | 0.5 | 1177 | 0.153 | 7.00 | 110 |
| 20 | 5 | 0.5 | 1070 | 0.139 | 6.37 | 100 |
| 20 | 3 | 0.5 | 642 | 0.083 | 6.37 | 60 |
| 19 | 2.7 | 0.5 | 548.91 | 0.071 | 6.05 | 51.3 |
| 18 | 2.5 | 0.5 | 481.5 | 0.063 | 5.73 | 45 |

As can be seen from the calculations, a ring having a diameter of about 7 mm, a height of 5 mm and a mass of about 1.18 g closely matches the specific heat of the TGA crucible. The surface area of the ring will be equal to that of the crucible (about 110 mm$^2$), which should result in a similar heat exchange between both the crucible and reference ring. Thus, depending on the thermal properties of the crucible used, a reference sensor may be designed to match the thermal properties of the crucible.

EXAMPLE 3

Temperature Gradient Measurements

A specific STA performance criterion is flatness and repeatability of differential thermal analysis baselines. Non ideal (non-flat) baselines occur due to mismatch in thermal properties of reference and sample side and to temperature gradients in the furnace itself. Temperature gradients in the furnace were determined, both in a mathematical thermal model and by actual temperature measurements. Both horizontal and vertical temperature gradients were determined, at several temperature set levels (up to 1000° C.). With the vertical temperature gradient measurement, it was decided to put the "center" of the sensor, that is the separation gap in between the lower side of crucible and crucible holder and the upper side of the reference ring just in the flat zone of the vertical temperature gradient (that is, at a height of 8.5 mm from the bottom of the furnace. As the vertical temperature gradient is typically symmetrical, the temperature fall is mainly compensated.

Figure 18:
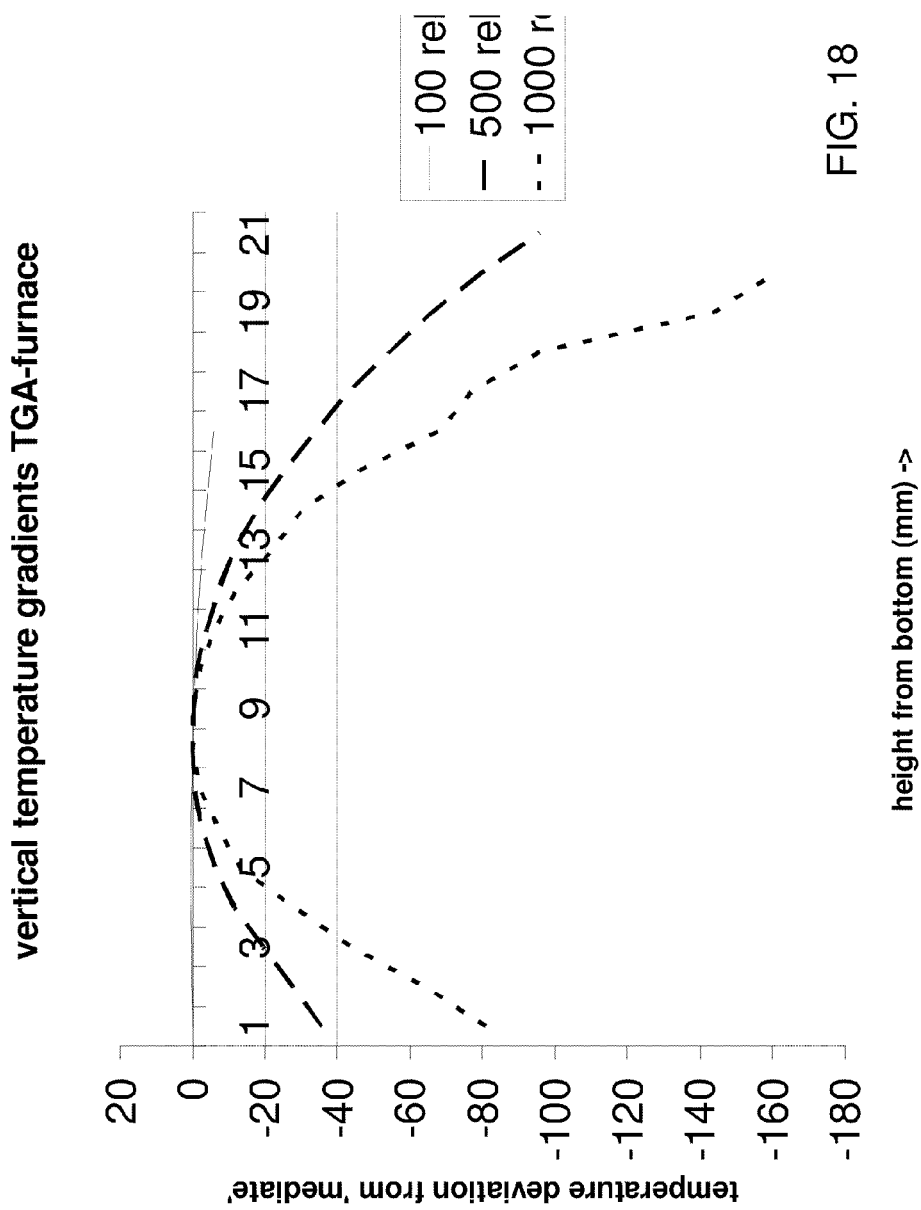
FIGS. 18 and 19 are graphs showing temperature measurements, in accordance with certain examples.
Figure 19:
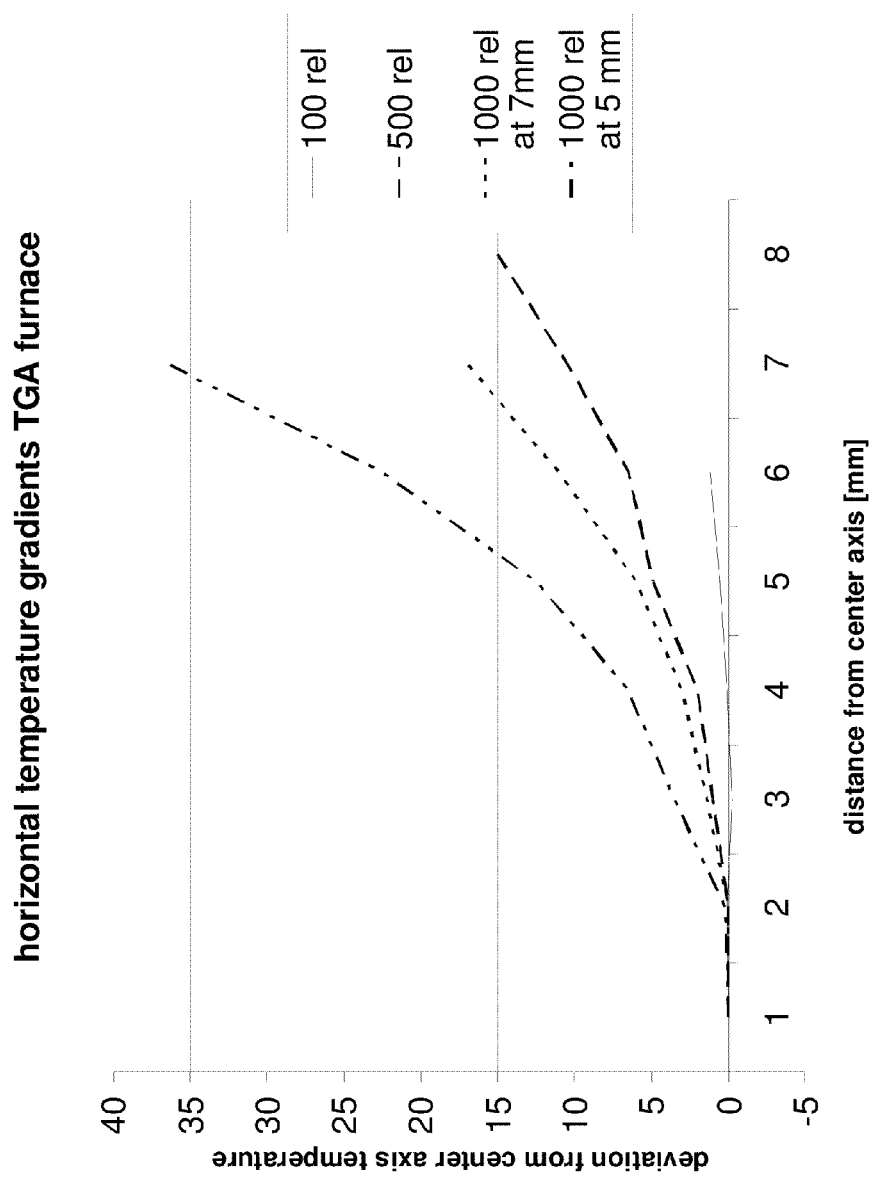

The sensor included a support member that was 75 mm long and 1.6 mm in diameter. The center of the sensor was placed approximately 8.5 mm from the bottom of a furnace. The furnace actually used had an inner diameter of 13 mm, an outer diameter of 20 mm and a height of 25 mm. The reference sensor was about 7 mm wide (outer diameter), 6 mm wide (inner diameter) by about 5 mm long and was a hollow cylindrical ring. The inner surface of the reference sensor ring was placed about 0.25 mm from the outer surface of the sample support. A crucible that was 5 mm tall and 7 mm in diameter was placed on the sample support. A balance connector that was about 3 mm by about 3 mm was used to couple the single stem sensor to a balance. Graphs of the measured second sensor furnace temperature gradients are shown in FIGS. 18 and 19. In the graphs, "100 rel" refers to temperature deviations related to original sample position (which was based on the location in the furnace of a sample in the original Pyris6 TGA—the instrument in which the furnace originally was used) at a set temperature of 100° C., "500 rel" refers to temperature deviations related to original sample position at a set temperature of 500° C., and "1000 rel" refers to temperature deviations related to original sample position at a set temperature of 1000° C.

EXAMPLE 4

Figure 20:
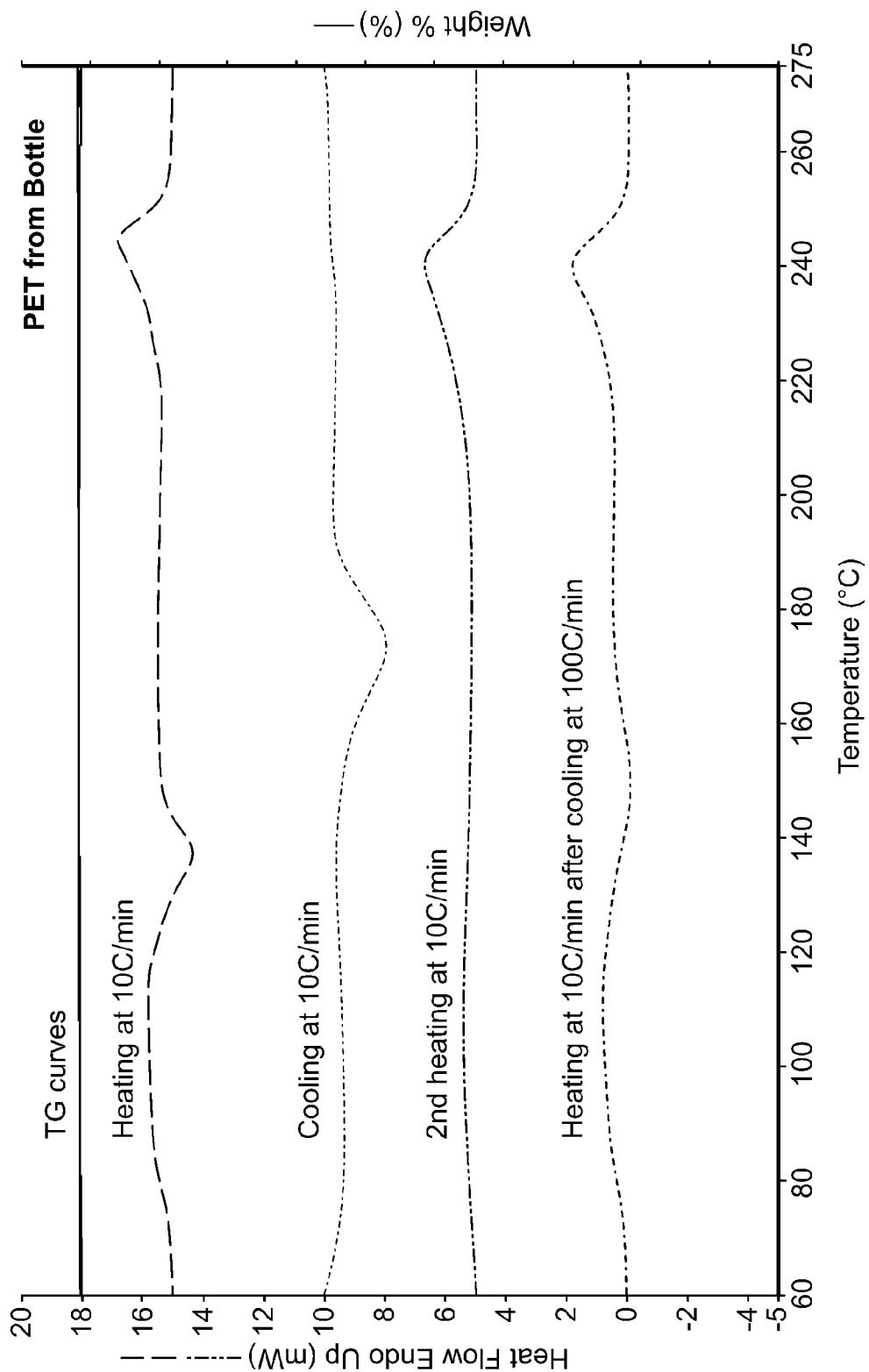
FIGS. 20-25 are graphs showing the results of various thermal analyses, in accordance with certain examples.

The thermal properties of polyethylene terephthalate (PET) were measured on a STA 6000 (commercially available from PerkinElmer Life and Analytical Sciences, Inc.) using 10 mg of PET, a nitrogen gas rate of 20 mL/minute, a heating rate of 10° C./minute and a cooling rate of 10° C./minute and 100° C./minute. The results are shown in FIG. 20.

EXAMPLE 5

Figure 21:
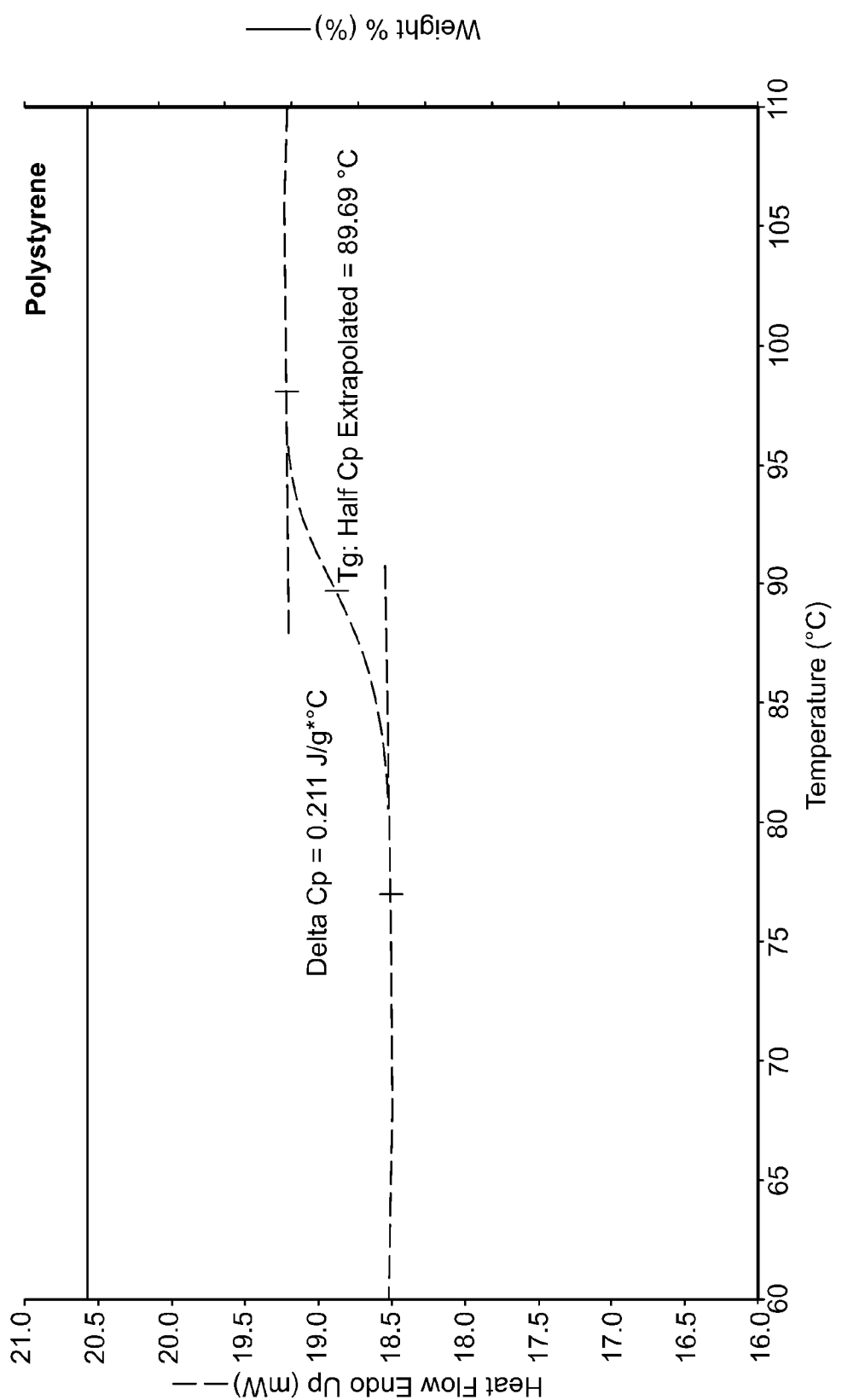

TG and DSC measurements were performed on polystyrene using a STA 6000 (commercially available from PerkinElmer Life and Analytical Sciences, Inc.) with 18 mg of polystyrene, a nitrogen gas rate of 20 mL/minute, and a heating rate of 10° C./minute. The results are shown in FIG. 21.

EXAMPLE 6

Figure 22:
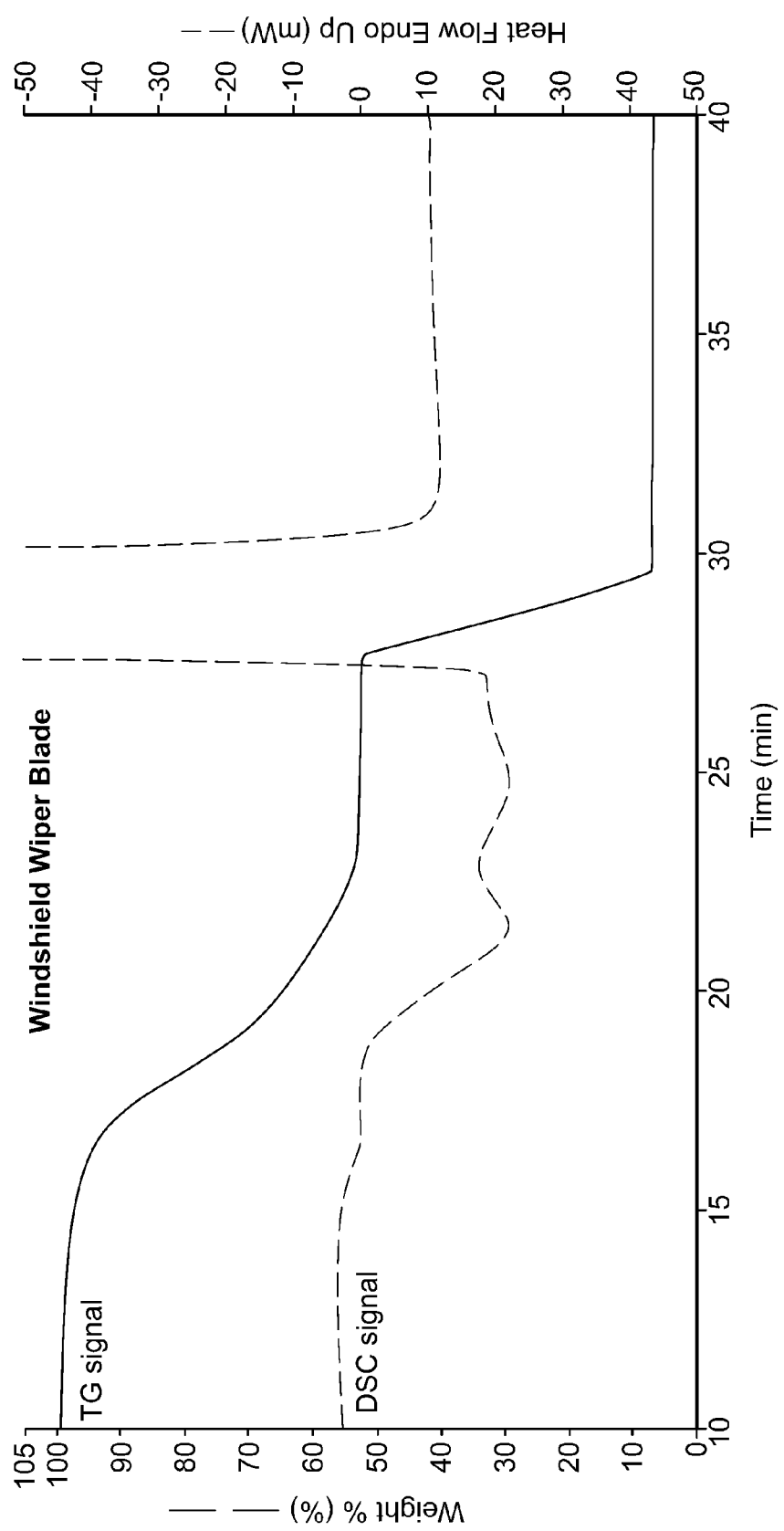

TG and DSC measurements were performed on wiper blade butyl rubber using a STA 6000 (commercially available from PerkinElmer Life and Analytical Sciences, Inc.) with 16 mg of sample, a nitrogen gas rate of 20 mL/minute, which was switched at 600° C. to oxygen at 50 mL/minute to burn off the carbon black and measure the filler content. A heating rate of 20° C./minute was used. The results are shown in FIG. 22.

EXAMPLE 7

Figure 23:
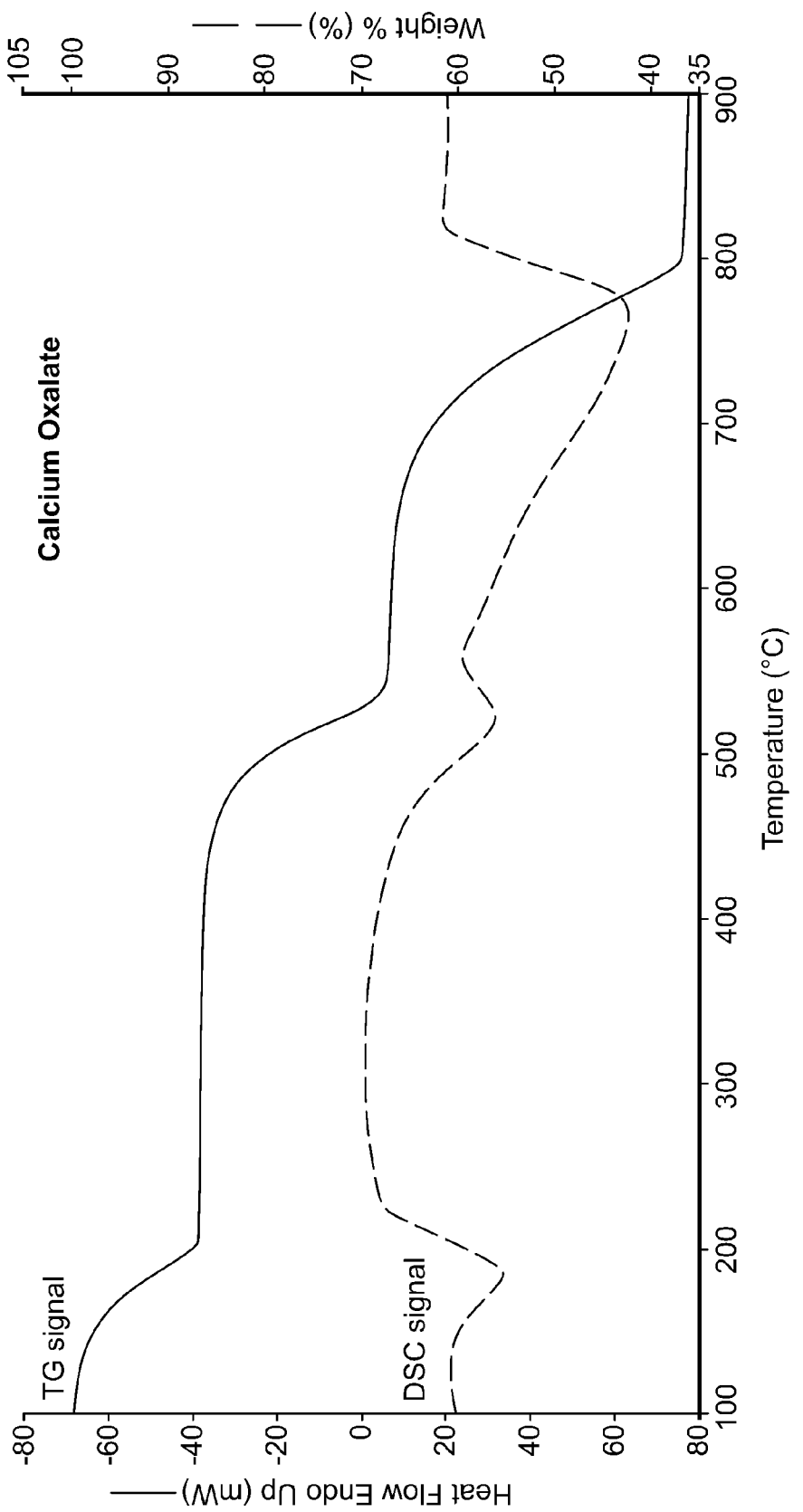

TG and DSC measurements were performed on calcium oxalate using a STA 6000 (commercially available from PerkinElmer Life and Analytical Sciences, Inc.) with 15 mg of sample, a helium gas rate of 40 mL/minute, and a heating rate of 20° C./minute. Calcium oxalate sample is often used to confirm the performance of a simultaneous thermal analyzer. The results are shown in FIG. 23. The first step is representative of water, the second step is representative of carbon monoxide, and the third step is representative of carbon dioxide.

EXAMPLE 8

Figure 24:
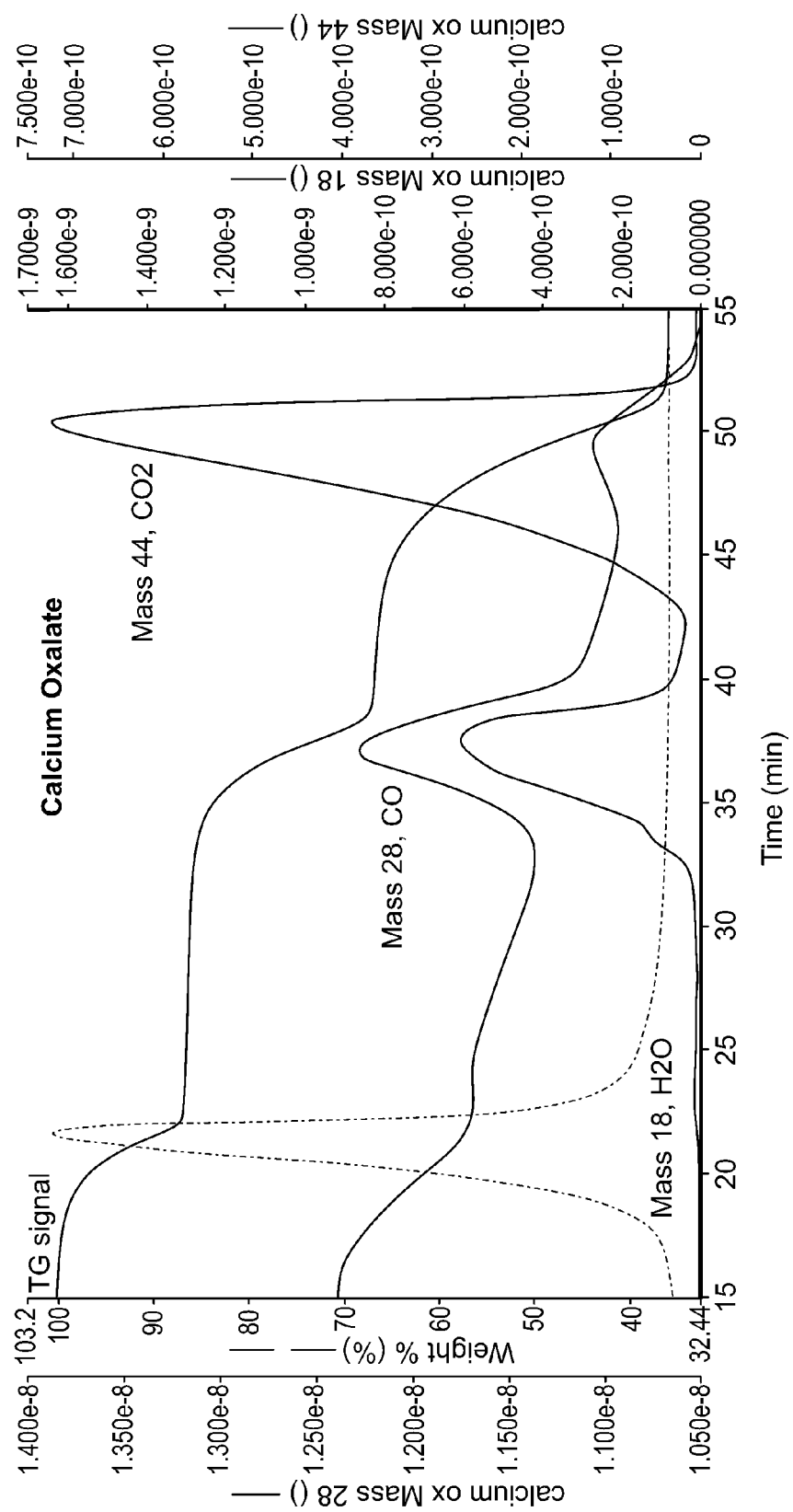

TG and MS measurements were performed on calcium oxalate using a STA 6000 (commercially available from PerkinElmer Life and Analytical Sciences, Inc.) with 15 mg of sample, a helium gas rate of 40 mL/minute, and a heating rate of 20° C./minute. The STA 6000 was also coupled to a mass spectrometer (a Pfeiffer Thermostar MS). A short transfer line (which was heated) between the capillary of the MS and the STA 6000 provided sample from the STA 6000 to the MS. The results are shown in FIG. 24. The mass spectrometer analysis provided the detected weights of 18, 28 and 44, which are representative of water, carbon monoxide and carbon dioxide, respectively.

EXAMPLE 9

Figure 25:
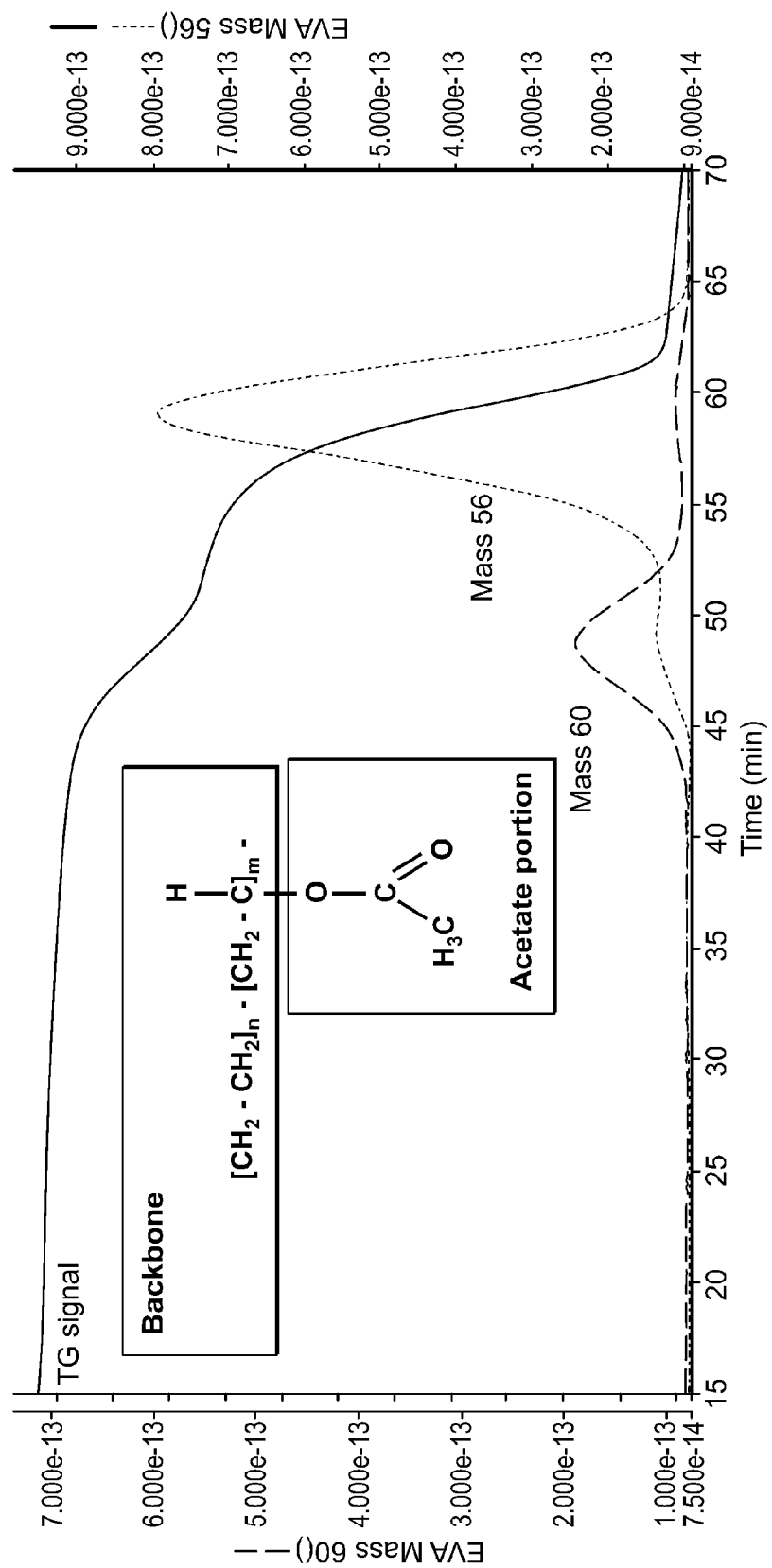

TG and MS measurements were performed on ethyl vinyl acetate using a STA 6000 (commercially available from PerkinElmer Life and Analytical Sciences, Inc.) with 19 mg of sample, a helium gas rate of 40 mL/minute, and a heating rate of 20° C./minute. The STA 6000 was also coupled to a mass spectrometer (a Pfeiffer Thermostar MS). A short transfer line (which was heated) between the capillary of the MS and the STA 6000 provided sample from the STA 6000 to the MS. The results are shown in FIG. 25. The acetate portion is represented as mass 60, and the backbone portion is represented as mass 56 (see inset of FIG. 25).

When introducing elements of the examples disclosed herein, the articles "a," "an," and "the" are intended to mean that there are one or more of the elements. The terms "comprising," "including" and "having" are intended to be open ended and mean that there may be additional elements other than the listed elements. It will be recognized by the person of ordinary skill in the art, given the benefit of this disclosure, that various components of the examples can be interchanged or substituted with various components in other examples.

Although certain features, aspects, examples and embodiments have been described above, additions, substitutions, modifications, and alterations of the disclosed illustrative features, aspects, examples and embodiments will be readily recognized by the person of ordinary skill in the art, given the benefit of this disclosure.

What is claimed is:

1. A sensor comprising:
   a support member;
   a sample sensor coupled to the support member and comprising a sample support electrically coupled to a first set of interconnects; and
   a reference sensor coupled to the support member and comprising a ring coupled to a second set of interconnects, in which the ring is positioned adjacent to and surrounding at least a portion of the sample support of the sample sensor.

2. The sensor of claim 1, further comprising a connector coupled to the support member, the connector configured to couple the sensor to a balance.

3. The sensor of claim 1, further comprising a controller coupled to the first set of interconnects and the second set of interconnects.

4. The sensor of claim 1, in which the sample support and the ring of the reference sensor are both platinum.

5. The sensor of claim 1, wherein the reference sensor is configured to provide a reference signal without the addition of an external reference material.

6. The sensor of claim 1, in which the sample support comprises a concave surface configured to receive a crucible comprising a sample.

7. The sensor of claim 1, in which the ring of the reference sensor is a cylindrical ring with an inner surface positioned less than 0.5 mm from an outer surface of the sample support.

8. The sensor of claim 7, in which the ring comprises an outer diameter of 6 mm to 8 mm and an inner diameter of 5 mm to 7 mm.

9. A system for simultaneous thermal analysis, the system comprising:
   a heating system comprising a furnace thermally coupled to a sensor comprising
      a support member;
      a sample sensor coupled to the support member and comprising a sample support electrically coupled to a first set of interconnects; and
      a reference sensor coupled to the support member and comprising a ring coupled to a second set of interconnects, in which the ring is positioned adjacent to and surrounding at least a portion of the sample support of the sample sensor; and
   a controller coupled to the heating system and configured to receive signals from the first and second set of interconnects of the sensor.

10. The system of claim 9, further comprising a gas control system coupled to the heating system.

11. The system of claim 9, further comprising an analytical device coupled to the simultaneous thermal analysis system, the analytical device selected from the group consisting of a mass spectrometer, an infrared spectrometer, a gas chromatograph and combinations thereof.

12. The system of claim 9, further comprising a computer system coupled to the simultaneous thermal analysis system.

13. The system of claim 9, further comprising an autosampling system coupled to the heating system.

14. The system of claim 9, further comprising a balance coupled to the sensor.

15. The system of claim 14, in which the simultaneous thermal analysis system is configured for thermogravimetric analysis and at least one of differential thermal analysis and differential scanning calorimetry.

16. A method of measuring thermal properties of a sample comprising:
   placing a sample on a sample support of a sensor in a furnace, the sensor comprising a sample support and a reference sensor adjacent to and surrounding at least a portion of the sample support;
   altering the temperature in the furnace to promote a physical or chemical change in the sample; and
   measuring the physical or chemical change in the sample using the sample sensor and the reference sensor.

17. The method of claim 16, further comprising measuring the physical or chemical change without adding an external reference material to the reference sensor.

18. The method of claim 16, further comprising measuring a change in mass of the sample and a change in temperature of the sample during the temperature altering step.

19. A method of facilitating measurement of thermal properties of a sample comprising providing a sensor configured with a support member, a sample sensor coupled to the support member and comprising a sample support electrically coupled to a first set of interconnects, and a reference sensor coupled to the support member and comprising a ring coupled to a second set of interconnects, in which the ring is positioned adjacent to and surrounding at least a portion of the sample support of the sample sensor.

* * * * *